(12) United States Patent
Nussinovich et al.

(10) Patent No.: US 8,932,634 B2
(45) Date of Patent: Jan. 13, 2015

(54) HYDROCOLLOID CARRIER BEADS WITH INERT FILLER MATERIAL

(75) Inventors: Amos Nussinovich, Rehovot (IL); Avi Gal, Ganei Yohanan (IL)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 1422 days.

(21) Appl. No.: 12/304,997

(22) PCT Filed: Jun. 17, 2007

(86) PCT No.: PCT/IL2007/000733
§ 371 (c)(1),
(2), (4) Date: Sep. 3, 2009

(87) PCT Pub. No.: WO2007/144894
PCT Pub. Date: Dec. 21, 2007

(65) Prior Publication Data
US 2010/0015192 A1    Jan. 21, 2010

Related U.S. Application Data

(60) Provisional application No. 60/813,691, filed on Jun. 15, 2006.

(51) Int. Cl.
| A61K 9/14 | (2006.01) |
| A61K 9/50 | (2006.01) |
| A01N 25/08 | (2006.01) |
| A61K 9/16 | (2006.01) |

(52) U.S. Cl.
CPC ............. *A61K 9/1652* (2013.01); *A61K 9/1611* (2013.01); *A61K 9/1694* (2013.01)
USPC ............................ 424/489; 424/496; 424/409

(58) Field of Classification Search
None
See application file for complete search history.

(56) References Cited

U.S. PATENT DOCUMENTS

| 4,818,530 A | | 4/1989 | Marois |
| 5,089,407 A | * | 2/1992 | Baker et al. .................... 435/179 |
| 5,662,840 A | * | 9/1997 | Thomas et al. ................. 264/12 |
| 6,297,033 B1 | | 10/2001 | Van Rijn |

(Continued)

FOREIGN PATENT DOCUMENTS

| GB | 2 399 499 A | 9/2004 |
| WO | 99/53902 A1 | 10/1999 |

(Continued)

OTHER PUBLICATIONS

Buckley et al., "Diltiazem-A reappraisal of its pharmacological and therapeutic use" Drugs 39(5): 757-806 (1990) abstract.

(Continued)

*Primary Examiner* — Carlos Azpuru
*Assistant Examiner* — Casey Hagopian
(74) *Attorney, Agent, or Firm* — Browdy and Neimark, PLLC.

(57) ABSTRACT

This invention discloses carrier beads comprising a hydrocolloid polymer comprising at least one inert filler material, wherein the at least one filler material provides improved properties including increased mechanical strength and/or reduced porosity relative to a bead without said at least one filler. The beads are useful per se or for delivery of active agents. Methods for preparation of the beads and the uses thereof are described particularly for controlling the rate of release an active agent from said bead.

20 Claims, 8 Drawing Sheets

(56) References Cited

U.S. PATENT DOCUMENTS

| | | | |
|---|---|---|---|
| 6,589,328 B1 | 7/2003 | Nussinovitch | |
| 6,649,191 B1* | 11/2003 | Tester et al. | 424/488 |
| 7,022,313 B2 | 4/2006 | O'Connor | |
| 7,189,275 B2 | 3/2007 | Pildysh | |
| 2003/0224022 A1 | 12/2003 | Nussinovitch | |
| 2004/0131690 A1* | 7/2004 | Lynch | 424/489 |
| 2009/0324568 A1* | 12/2009 | Huguet et al. | 424/94.1 |

FOREIGN PATENT DOCUMENTS

| | | | |
|---|---|---|---|
| WO | 01/30145 A1 | 5/2001 | |
| WO | 03/018186 A1 | 3/2003 | |
| WO | 2004/032901 A1 | 4/2004 | |
| WO | 2004/043140 A2 | 5/2004 | |
| WO | 2005/072709 A2 | 8/2005 | |
| WO | 2005/079703 A1 | 9/2005 | |
| WO | WO 2006030297 A1 * | 3/2006 | |

OTHER PUBLICATIONS

El-Kamel., "Alginate-diltiazem hydrochloride beads: optimization of formulation factors, in-vitro and in-vivo availability" J Microencapsul 20(2): 221-225 (2003).

Ferreira Almeida and Almeida., "Cross-linked alginate-gelatin beads: a new matrix for controlled release of pindolol" J Controlled Release 97(3): 431-439 (2004).

Gal and Nussinovitch., "Hydrocolloid Carriers with filler inclusion for diltiazem hydrochloride release" J Pharm Sci 96 (1): 168-178 (2007).

Hack and Selenka., "Mobilization of PAH and PCB from contaminated soil using a digestive tract model" Toxicol Lett 88(1-3): 199-210 (1996).

Haglund et al., "Dissolution controlled drug-release from agarose beads" Drug Dev Ind Pharm 20(6): 947-959 (1994).

Homsy et al., "Metabolism of diltiazem in hepatic and extrahepatic tissues of rabbits: in-vitro studies" Pharm Res 12(4): 609-614 (1995).

Hwang et al., "Release characteristics of ibuprofen from excipient-loaded alginate gel beads" Int J Pharm 116(1): 125-128 (1995).

Kedzierewicz et al., "Effect of the formulation in-vitro release of propranolol from gellan beads" Int J Pharm 178(1): 129-136 (1999).

Leopold., "Coated dosage forms for colon-specific drug delivery" Pharm Sci Technolo Today 2(5): 197-204 (1999).

Liu and Krishnan., "Alginate-pectin-poly-L-lysine particulate as a potential controlled release formulation" J Pharm Pharmacol 51(2): 141-149 (1999).

Nussinovitch et al., "Apparatus for the continuous monitoring of changes in shrinking gels" Food Hydrocolloids 10(2): 137-141 (1996).

Panchgnula and Thomas., "Biopharmaceutics and pharmacokinetics in drug research" Int J Pharm 201(2): 131-150 (2000).

Tapia et al., "Comparative studies on polyelectrolyte complexes and mixtures of chitosan-alginate and chitosan-carrageenan as prolonged diltiazem clorhydrate release systems" Eur J Pharm Biopharm 57(1): 65-75 (2004).

Toti and Aminabhavi., "Modified guar gum matrix for controlled release of diltiazem hydrochloride" J Controlled Release 95(3): 567-577 (2004).

Zohar-Perez et al.,"Irregular surface-textural features of dried alginate-filler beads" Food Hydrocolloids 18(2):249-258 (2004).

Zohar-Perez et al., "Structure of dried cellular alginate matrix containing fillers provides extra protection for microorganisms against UVC radiation" Radiat Res 160(2): 198-204 (2003).

* cited by examiner

HYDROCOLLOID CARRIER BEADS WITH INERT FILLER MATERIAL

FIELD OF THE INVENTION

This invention relates to hydrocolloid carrier beads with inert filler materials having increased mechanical strength and/or reduced porosity and their uses in slow release of active agents in situ, and to methods of forming these carrier beads and applications thereof.

BACKGROUND OF THE INVENTION

The administration of active agents in medical, veterinary or agricultural applications requires formulations that afford suitable availability of the active agent with minimal doses and an acceptable level of adverse effects.

Classically, physicians have administered toxic medicaments to patients in relatively high dosages, with spaced-apart dosage regimens. The percent efficiency of such administration is relatively low. Furthermore, there is often a limit on the cumulative quantity of a drug that can be administered to the patient. There has thus been a trend, over the last few decades, to attempt to provide slow release compositions of the medicaments or drugs.

The administration of active agents in agriculture suffers from the same trends as noted above with regard to medicaments. Typically a pesticide or other active agent is administered to the agricultural environment in large quantities but with little effect to the target organism and detrimental effects to many other non-targeted organisms. There is thus a need to provide agricultural agents in effective slow release, non-toxic forms with low risk:benefit ratios.

Different types of slow-release formulations of drugs and agricultural agents have been investigated, including, but not limited to, liposomes, inert carriers, and colloidal carriers.

It is known in the art that a variety of hydrocolloids have been studied for their potential use as carriers for the controlled release of compounds, including drugs and agrochemical compounds, such as those used for pest control. Several studies have focused on alginate-based carriers, revealing some difficulties. For one, the loading efficacy of the active ingredient (drug, agro-chemical compound) is too low due to its leakage into the cross-linking solution (1, 2).

The evaluation of drug-carrier efficacy is not simple, because release profiles vary with pH (1, 3). Active compound solubility can be influenced by the pH of the dissolution medium (4), as can the stability of other components of the formulation. For example, Eudragit, which is soluble at a pH above 6, is often used as a coating material in extended drug-release formulations (5). Therefore, carriers should be examined in a continuous simulated ambient model which, for orally administered drugs, is the gastrointestinal model and, for agro-chemical uses, is soil. Combinations of alginate with other hydrocolloids have also been reported (6, 7). Less information can be found on carriers based on guar gum (8), and even fewer studies have focused on gellan, agar and agarose or other hydrocolloid gelling agents which have the potential for carrier manufacturing (9, 10).

Formulations based on hydrocolloids may have some advantages over other sustained-release formulations. For instance, different structures can be obtained upon dehydration of the hydrocolloid formulations. These structures can be modified by the drying conditions and formulation composition. Structural characteristics, such as porosity, may affect the penetration rate of liquid into the formulations and thus modify the release pattern of the drug.

Moreover, the stability and physical properties (dimensions, strength, etc.) of various hydrocolloids are affected by factors such as swelling in water, pH value, and enzymes, and therefore vary in different parts of the gastrointestinal tract. Changes in the physical properties of the formulations may also lead to different drug-release patterns in different parts of the gastrointestinal tract.

Thus, hydrocolloids can be used as carriers for the controlled release of drugs. In addition, hydrocolloid-formulation preparation procedures are generally quite simple and the cost of such materials is low (11).

U.S. Pat. No. 4,818,530 to Marois, et al. discloses pellets containing living biocontrol fungi in an alginate mixture. Various organic and inorganic fillers, preferably pyrophillite, are disclosed among a long list of additional optional adjuvants that may be incorporated into the formulations. The fillers are an optional ingredient, and not disclosed as imparting any requisite structural or mechanical properties to the pellets.

U.S. Pat. No. 6,297,033, to one of the inventors of the present invention and co-workers, discloses permeable polymeric beads which contain a combination of fermentative and denitrifying bacteria and a carbon source, for use in a system for nitrate removal from aquariums. The carbon source used is preferably potato starch, and is not disclosed as imparting any structural or mechanical properties to the beads.

U.S. Pat. No. 6,589,328 to one of the inventors of the present invention, discloses hydrocolloid sponges produced by preparing a gel of a hydrocolloid, and either sealing it in a closed vessel with a liquid of similar composition, pressurizing the vessel and abruptly releasing the pressure, followed by freeze drying, or by incorporating in such a gel a suitable microorganism, such as a yeast, and inducing fermentation in the presence of a suitable nutrient medium, so that the carbon dioxide formed results in expansion and foam formation, which is processed to the final product.

Zohar-Perez, et al. (20) disclose irregular textural features of dried alginate-filler beads, having up to 0.5% (w/w) of bentonite or kaolin as fillers. These beads are further reported to provide extra protection for microorganisms against UV radiation (24).

US Patent Application Publication Number 2003/0224022 to one of the inventors of the present invention, discloses hydrocolloid cellular solid matrices that are useful as carriers for a variety of substances.

U.S. Pat. No. 7,022,313, to O'Connor, et al., discloses new compositions formed from the combination of an active substance with a hydrogel carrier moiety. The compositions are suitable for use in high-velocity transdermal particle injection techniques. Methods of providing the new compositions are also provided. In addition, methods for administering pharmacologically active agents to a subject are provided. These methods are useful for delivering drugs, biopharmaceuticals, vaccines and diagnostics agents.

U.S. Pat. No. 7,189,275, to Pildysh, describes a permeable composition, a controlled release product, and methods for producing the permeable composition and controlled release product. The permeable composition includes a matrix material, a particulate filler material, and interfacial passageways between the matrix material and the particles of filler material. The matrix material may include a substrate material and a carrier material. The controlled release product is formed by coating a substrate material with at least one layer of the permeable composition. The methods include the steps of applying a degradable surface treatment material to the particles of filler material and then dispersing the surface treated filler material throughout the matrix material so that degradable interfaces are provided between the matrix material and the particles of filler material.

After the priority date of the present application, the inventors published a report on hydrocolloid carriers with filler inclusion for use in slow release of the pharmaceutical agent diltiazem hydrochloride (25). Diltiazem hydrochloride is a calcium antagonist used to moderate systemic hypertension. Anti-arrhythmic effects of the drug control the ventricular response to atrial fibrillation and flutter. This compound is also used for the treatment of stable and unstable angina pectoris. Although most of the administered drug dose is absorbed (90%), its bioavailability only reaches 30 to 65% because of a high first-pass effect, mainly in the liver and the gastro-intestinal tract (12). Diltiazem hydrochloride has a short plasma half-life of 3 to 4 h (13, 14) and is taken 3 to 4 times a day. Therefore, controlled/sustained-release formulations for diltiazem hydrochloride are needed.

There thus remains an unmet need for safer, more efficient and more effective ways of delivering medicaments to patients and agricultural agents to a specific organism or crop in the environment.

SUMMARY OF THE INVENTION

The present invention relates to hydrocolloid beads comprising an inert filler, having improved properties compared to beads having the same composition without the filler. The beads of the invention may be used for carrying active agents. Further provided are methods for preparation of the beads and uses thereof.

This invention is based on the finding that hydrocolloid-based beads have improved properties when, in addition to the hydrocolloid material, they also contain inert filler material. These improved properties, as compared to beads without the filler, are: decreased rate of disintegration of the bead and, where the bead contains an active agent to be released, a decreased rate of release of the active agent from the bead; improved compressibility; increased durability of the bead in solution and decreased porosity of the carrier.

The active agent may be a medicinally active agent, an agro-chemical used in agriculture, an agent used in the food industry or a chemical or biological agent used in chemical or biotechnological manufacture.

In addition, the beads per se, comprising a hydrocolloid and an inert filler without any active ingredient, may also have beneficial properties. They may be used for absorbing certain compounds and thus lowering the levels of those compounds in the body, e.g. lowering cholesterol levels and treating overdoses of drugs and toxins. In agriculture, compositions comprising the beads themselves, occasionally referred to hereinafter as "empty" beads, are beneficial for example, in the decomposition of chitosan carriers, used to encourage the growth of beneficial microorganisms, notably fungi, in soil.

Thus, by one aspect, the present invention provides hydrocolloid beads comprising an inert filler material, wherein the inert filler is present in an amount greater than 2% (w/w) preferably greater than 5% (w/w), more preferably about 10% or more of the wet weight of the beads. According to certain embodiments, the filler should constitute about 10 to 15% (w/w) of the wet weight of the bead. Accordingly, after drying the beads, the filler will constitute around 50-70% (w/w) of the dried bead.

Preferably the filler should be in a quantity sufficient to change at least one of the following bead parameters as compared to a bead having the same components and prepared in the same manner without the filler:

a) slower disintegration rate of an active agent in a fluid;
b) slower rate of release of an active agent present in the bead relative to the release of the free active agent;
c) increased mechanical strength of the bead after freeze-drying or other methods of dehydration;
d) increased compressibility of the hydrocolloid bead;
e) reduced porosity of a hydrocolloid bead;
f) increased surface roughness of the bead (in several compositions).

There is thus provided, according to one aspect of the present invention, a hydrocolloid carrier bead comprising a hydrocolloid polymer and at least one inert filler material, wherein the at least one filler material provides a least one property selected from increased mechanical strength, increased compressibility and reduced porosity compared to a bead having the same composition without the at least one filler.

According to some embodiments, the polymer is selected from agar, agarose, pectin, carrageenan, alginate, gelatin, gellan, konjak mannan, and a combination of xanthan gum and locust bean gum (LBG).

Typically the polymer is present in a weight percent ranging from 0.02 to 20% (w/w) of the wet beads. According to some embodiments, the polymer is present in a weight percent of 0.5 to 15% (w/w) of the wet weight. According to some embodiments, the weight percent of the polymer in the beads is 1-3%, although the appropriate percentage of the polymer will be determined for the actual polymer used, as is well known to one of skill in the art. After drying, the hydrocolloid polymer will correspondingly rise and, typically, will comprise a weight percent of 0.1 to 30% of the dry beads.

In some embodiments, the polymer comprises alginate. The alginate typically will be present in a weight percent ranging from 1-3%. In other embodiments, the polymer comprises agarose. Agarose typically will be present in a weight percent ranging from 0.02 to 5% of the wet weight of the beads, or suitably 1-3%.

According to some embodiments, the at least one filler material comprises grains or particles in the nanoparticle or microparticle size range. Typically, though not exclusively, the filler will have particles in the size range of 0.1 µm to 100 µm.

The at least one filler material may be selected from the group consisting of biodegradable and non-biodegradable inert particles. According to some embodiments, the filler is non-biodegradable. For some applications, non-biodegradable fillers are preferable since they do not serve as a substrate that supports microorganisms. According to some embodiments the filler is insoluble in aqueous media, and will form a dispersion in the hydrocolloid gel.

The at least one filler may be selected from talc, kaolin, calcium carbonate, silicon dioxide, titanium dioxide, alumina, powdered cellulose, microcrystalline cellulose, hydroxypropyl methylcellulose and a starch such as potato or corn starch. Combinations of these fillers are also useful under certain circumstances.

In some embodiments, the at least one filler material is present in a weight percent of up to 70% (w/w) of the dried bead. In other embodiments, the filler is present in a weight percent of up to 50% (w/w) of the dried bead.

The carrier bead may be used per se or may further comprise at least one active agent. The active agent may be selected from a medicinally active agent, a chemical or biological agent and an agriculturally active agent. According to some embodiments, the medicinally active agent is selected from a drug, a pro-drug, a combination of drugs, a diagnostic agent and an imaging agent used in therapy or diagnosis. The drug is selected from a water-soluble drug and a water-insoluble drug. In cases where the drug is a water-insoluble drug, it may be provided in an oil, a fat or an emulsion.

In some embodiments of the present invention, the agriculturally active agent is selected from an agro-chemical compound used for control of pests, a fertilizer, a biological agent or compound. According to preferred embodiments the biological agent is other than an active microorganism used for biological control of a pest or a disease.

The carrier beads of the present invention include at least one filler material, which is adapted to reduce the rate of the release of the at least one active agent from the bead relative to a bead without the at least one filler.

There is also provided according to some additional embodiments of the present invention a method for forming a plurality of carrier beads, the method comprising:

(a) mixing at least one filler material with a hydrogel solution to form a preparative bead solution, suspension or dispersion;

(b) forming a plurality of carrier beads comprising a hydrocolloid polymer and at least one inert filler material from the preparative bead solution, suspension or dispersion by inducing the beads to undergo at least one of hydrogen bond formation and a cross-linking reaction, wherein the at least one filler material provides at least one property selected from increased mechanical strength, increased compressibility and reduced porosity compared to a bead having the same composition without the at least one filler.

The method may further comprise preparing a hydrogel solution comprising water and at least one hydrocolloid polymer prior to the mixing step (a). The at least one hydrogel material may be selected from agar, agarose, pectin, carrageenan, alginate, gelatin, gellan, konjak mannan, xanthan gum and locust bean gum, k-carrageenan and LBG, or combinations thereof. The at least one filler material may be selected from the group consisting of talc, kaolin, calcium carbonate, silicon dioxide, titanium dioxide, alumina, powdered cellulose, microcrystalline cellulose, and a starch, such as potato or corn starch. According to some embodiments the filler material is insoluble and/or non-biodegradable. For these embodiments the filler will be other than starch.

This hydrogel preparation step may be performed, for example, above the gelling temperature of the polymer, typically at 30-50° C. Typically, the mixing step is performed at 50-100° C. However, the actual temperature ranges used will be determined in accordance with the specific polymers used and the presence of active agents that may be temperature sensitive, as is known to one of skill in the art.

The mixing step may typically include mixing the at least one hydrogel material with at least one filler material in a weight ratio of the polymer to the filler in the range of 1:50 to 1:1. In the formation step, the cross-linking reaction may be induced in the presence of at least one type of cation, typically a univalent, bivalent or trivalent metallic ion. In certain embodiments, cross-linking can be performed by introducing suitable polysaccharides together, as is the case with k-carrageenan and LBG, or xanthan gum and LBG.

According to some embodiments, the method further comprises introducing at least one active agent during at least one of the mixing and forming steps. The at least one active agent is selected from a medicinally active agent, a chemical agent, a biological agent and an agriculturally active agent.

According to some embodiments, the method of the present invention produces carrier beads having a reduced porosity. Decreased porosity is advantageous in that it may diminish the rate of swelling of the carrier or slow the rate of fluid absorbance and is suitable to reducing the rate of release of the at least one active agent from the bead relative to a bead without the at least one filler. The medicinally active agent may be selected from a drug, a pro-drug, a combination of drugs, a diagnostic agent and an imaging agent used in therapy or diagnosis.

The method for forming the carrier beads may further comprise drying the carrier bead. The drying step may be performed by a method selected from freeze drying, vacuum drying, spray drying, fluidized bed drying, infra-red drying and solar drying.

According to some embodiments, the at least one bead has a mean size of 0.1 mm to 1 cm. These beads may also be size-reduced, if required. The size reducing step may provide particles of a mean size of 0.05-100 microns. Suitable methods of size reduction include ball mills, roller mills, pin-mills, disc mills and other means of grinding, shearing or milling as are known in the art. Additionally or alternatively, the method may further comprise compressing the beads.

Another aspect of the present invention provides pharmaceutical compositions comprising carrier beads according to the present invention. Also encompassed within the scope of the present invention are pharmaceutical compositions comprising a plurality of carrier beads produced according to the methods described herein.

Further embodiments of the present invention are directed to a method for treating a disorder comprising administering the pharmaceutical compositions of the present invention to a subject so as to treat the disorder.

These and other features of the invention will be better appreciated in conjunction with the figures, detailed description of preferred embodiments and examples which follow.

DETAILED DESCRIPTION OF THE INVENTION

Figure 1:
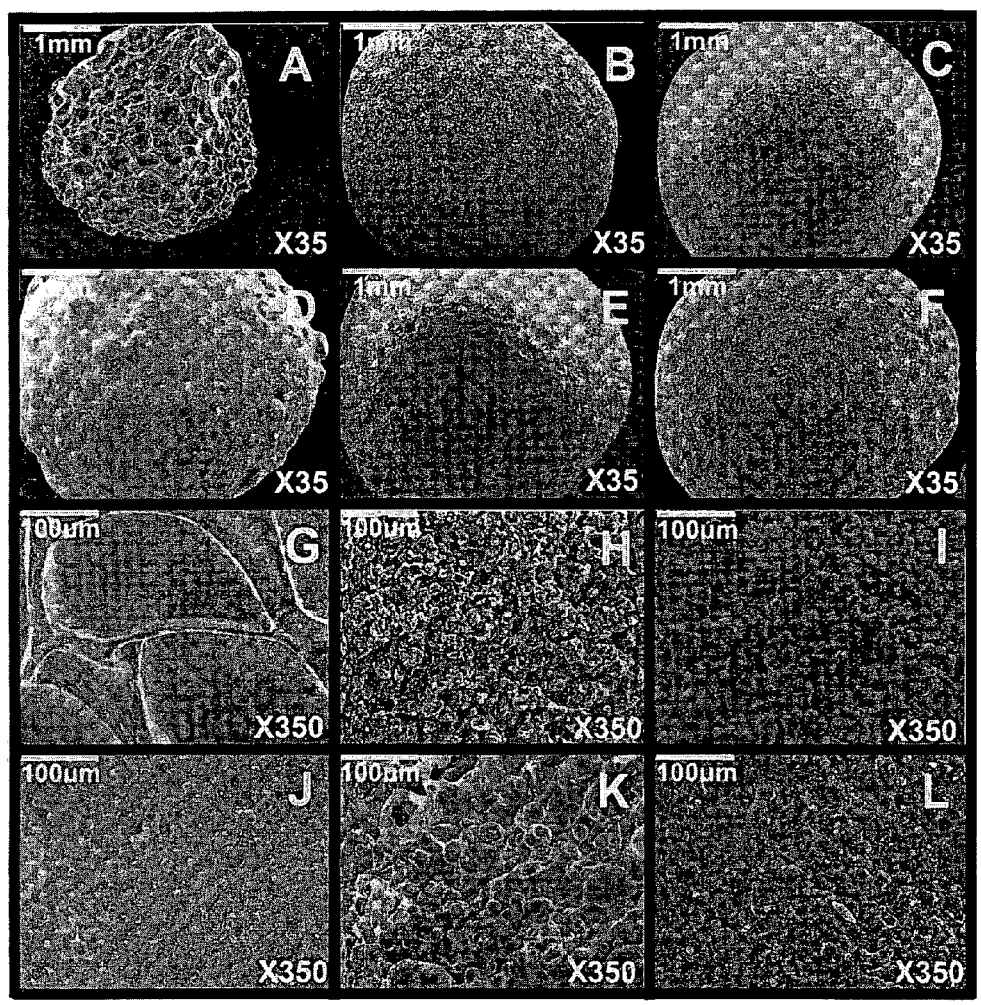
FIG. 1 shows electron microscope images of the outer surface of freeze dried agent carrier beads, in accordance with some embodiments of the present invention.

The present invention relates to hydrocolloid beads having improved properties imparted by the addition of inert filler material. These beads are useful per se or serve to carry active agents.

The term "bead" in the context of this invention refers to particulate material, having an irregular shape if milled or ground, or a shape selected from a spherical shape, a sphenoid shape, an ellipsoid shape and a teardrop-like shape. According to some embodiments, the beads have a size range of 100 microns to 1 cm and the size of the bead can be tailored according to the specific need. It will be appreciated that, after size reduction, the particles of the invention will generally be irregular in shape.

For example, smaller beads or carrier particles of less than 100 microns may also be obtained by grinding, shearing, milling, etc. Especially small carrier particles may be obtained by spray drying or by grinding using selected size reduction equipment such as ball mills, roller mills, pin and disc mills and the like. Larger beads in the range of 1 cm may be achieved by dropping and solidification.

The term "hydrocolloid material" refers to a hydrocolloid, a gum, or a gum resin being a water soluble polymer which, in the presence of an aqueous medium, forms a hydrocolloid gel upon cross-linking or by hydrogen bond creation. The material may be obtained from a natural source, may be a hydrocolloid from a natural source that has been chemically modified, or may be synthetic. Typically, the hydrocolloids are polymers and, more specifically, polysaccharide or polypeptides polymers. As used herein, the term "hydrocolloid material" includes both polysaccharides and proteins. For example, gelatin and casein are proteins that are regarded as hydrocolloids. The natural hydrocolloids may be of animal, vegetable or microbial origin. For example, agar is from algae, chitosan is derived from chitin extracted from crustaceans and gellan is a microbial hydrocolloid.

According to some embodiments of the invention, it is preferable to cross-link the hydrocolloid by using bivalent cations such as $Ca^{++}$, $Fe^{++}$, $Sr^{++}$, $Pb^{++}$ and $Ba^{++}$, or by using trivalent cations such as $Al^{+++}$. An alternative to cross-linking is to form hydrogen bonds, which in the case of agar or agarose are produced spontaneously in the gelling process. In the case of k-carrageenan, $K^+$, a monovalent ion, is used.

Non-limiting examples of hydropolymers suitable in the context of the present invention are agar, agarose, pectin, carrageenan, alginate, gelatin, gellan, konjak mannan, xanthan gum and locust bean gum (LBG), or a combination thereof. Xanthan and LBG gave a gel only when combined, whereas alone they are viscosity formers. On the other hand, k-carrageenan plus LBG (without a cross-linking agent) gave gels, i.e., they can together create a carrier gel. Other gelling agents, such as chitin, chitosan, curdlan, konjac and combinations thereof, can also be used for the gellification and bead formation process.

The term "filler" also referred to herein as an "inert filler" refers to an inactive organic or inorganic material that is typically used in the pharmaceutical industry to contribute to the medicament's bulk without affecting the activity of a drug. The fillers according to the invention, when the active agent is a drug, should be approved by the health authorities for administration to humans. Typically, these fillers are used in the form of powdered or granulated material, and are insoluble in aqueous media. They are dispersed in the hydrocolloid material prior to bead formation (e.g., spread and floating in the gum solution before solidification). Within the bead, they remain dispersed, and may appear in the bead in the form of an entrapped solid substance. Some of the fillers are soluble, including starches and some proteins, but these are unsuitable for many applications.

The original powder of filler used to prepare the beads should have grains ranging in size from 0.1 μm to 100 μm. For certain applications, it may be suitable to use micronized fillers or nanoparticles of the fillers. Preference of one filler over the other depends on tailoring the bead to its task. Without wishing to be bound by theory, the purpose of the filler, in accordance with this invention, is to change both the structure, the porosity and the texture of the bead. In some cases it is used to strengthen the bead, adding to its resistance to deformation. Changes within a bead can enable compression of the bead allowing it to retain partial porosity. Most fillers are inert and thus may be used to impart to the beads' properties that aid them to withstand harsh conditions.

Non-limiting examples of fillers are talc, kaolin, calcium carbonate, silicon dioxide, titanium dioxide, alumina, powdered cellulose, microcrystalline cellulose, hydroxy propyl methyl cellulose and starch, such as potato or corn starch. For some applications, non-biodegradable fillers are preferable or required, and, for these, proteins and starches will be excluded.

Typically, in the beads, the hydrocolloid material is 0.02 to 20% (w/w) preferably, 1 to 15% (w/w) more preferably and 1 to 3% (w/w) of the wet bead most preferably. It should be noted that, while for most hydrocolloids 1-3% w/w of the bead is the preferable range, for gelatin the preferable range is 15-20% w/w.

The present invention further discloses a pharmaceutical composition comprising the beads as described herein, carrying one or more active agents. The pharmaceutical composition may optionally comprise one or more pharmaceutically acceptable carrier or excipients, as are well known in the art of pharmaceutical sciences.

In pharmaceutical compositions comprising "empty" beads, the beads themselves induce a therapeutic effect. For example, they may reduce the level of a compound in excess by absorption thereof from the body of a subject. Empty beads may be used, for example, to reduce cholesterol levels, to detoxify subjects and to treat drug and medicament overdoses, especially in the framework of stomach pumping.

The present invention is further directed to a composition for use in agriculture comprising beads as described herein and an optional carrier. The purpose of the composition comprising the "empty" beads in agricultural uses is to facilitate absorption, especially of fertilizers, pesticides or toxic or noxious substances in the environment.

As a carrier in agricultural uses, the beads are used in the controlled release of the bead components into soil, for example, nutrients for beneficial microorganisms (fungi).

The present invention further concerns a composition comprising the beads as described herein, loaded with at least one active agent.

Typically, a dried bead may have a shelf life of at least two years. The term "active agent" refers to an organic or inorganic compound, a biological material, or complex of compounds, that affects, whether in vivo or in the environment, the ambient surrounding of the bead or the target in a desired manner, and for which slow and controlled release is beneficial.

By one embodiment, the active agent is a medicinally active agent, such as, but not limited to, a drug, a diagnostic agent or an imaging agent. The medicinally active agent may be any drug, pro-drug, combination of drugs, diagnostic agents, or imaging agents used in therapy or diagnosis. The drugs used in the beads of the present invention may be drugs with an improved medicinal activity in a controlled-release profile relative to a free form. The drug may be either water soluble or insoluble.

When a hydrophobic drug is used, the carrier beads may include a small quantity of oil and/or fat for solubilization of hydrophobic drug. The bead can be tailored for carrying any possible drug or materials specified above. The carrier biological agents may be selected from proteins, antibodies, peptides, nucleic acid based compounds and microorganisms that have a beneficial effect, such as probiotic bacteria.

According to some embodiments, the active agent may be diltiazem hydrochloride, provided in beads in which the amount of the filler is at least 10% w/w of the preparation media.

The medicament or pharmaceutical composition should preferably be adapted for oral administration, although other modes of administration are construed to be within the scope of the present invention. In the case of topical and mucosal administration, the beads may be incorporated into another matrix, such as a patch (glue). The patch may be used to place the beads in a sustained manner on the skin or mucosal tissue, as is known in the art.

By another embodiment, the active agent may be an agriculturally active agent such as an agro-chemical compound used for control of pests, as a herbicide, a fertilizer, a biological compound, or active microorganism used for biological control of pests and disease. In such a case, the composition may further comprise a carrier acceptable for agricultural use.

The "agriculturally active agent" may be any organic, inorganic or biological agent used in agriculture. This also includes biological agents, such as live agents, including microorganisms, used for control of pests, as a herbicide, as a fertilizer, or for supplying vitamins, minerals, pigments and preservatives to an agricultural environment. Some embodiments relate to the use in agriculture in the biological control of pests and disease, such as for biological control of root diseases and other diseases, to be applied to the soil, to a plant or to an aquatic environment, such as a pond, river or sea.

It should be noted that the requirements of an agriculturally active composition are different from a pharmaceutical composition. First, some harsh conditions that characterize the environment of drugs, especially orally administered drugs, such as low pH, do not characterize compounds administered to soil, plants or water. On the other hand, while the beads in the body are typically exposed to a constant moist environment, beads used for agricultural purposes are often exposed to drastically varying moisture levels and can revert from dry to wet stages.

In addition, the composition applied to soil is exposed to varying temperatures and to UV irradiation, as well as to microorganisms in soil, such as bacteria and molds, which are very different from the bacterial flora of the gastrointestinal (GI) tract.

Due to the different localized environments in which the beads are to release one or more active agents, the beads need to be designed differently according to their end application. Thus, compositions that are used for agriculture have to be tailored differently to those used in therapy.

By yet another embodiment, the active agent may be an agent used in the food industry or in the preparation of nutraceuticals such as vitamins, preservatives, pigments, taste enhancing compounds and functional food components.

According to yet another embodiment, the active agent may be a chemical, an enzyme, a reagent or a starting material for use in industry in chemical or biochemical reactions.

The present invention further concerns a method for the preparation of the above described beads, the method comprising:
A. providing hydrogel material dissolved in aqueous media;
B. adding filler material to the media;
C. forming beads; and
D. drying the beads.

Step (C), "forming beads," may be achieved in at least two ways. Typically, when beads are formed by hydrogen bond formation, the media may be dropped onto an appropriate fluid, such as cold water. In a particular embodiment, the molten polymer may be dropped through a thin oil layer into the hydrophilic medium (such as water, salt solution, etc.).

However, when beads are formed by cross-linking, the formation occurs by dropping the solution/suspension/dispersion/emulsion formed in step (B) to a bead forming (cross-linking) solution. The "bead forming" solution may be a cross-linking solution which is in excess (for example, when using alginate, gellan or chitosan) for producing a particulate bead. In another embodiment, the "bead forming solution" may have a cross-linking agent solution having an oil layer floating above it which helps form the beads, as in cases where agar or agarose is used.

The drying option depends on the application. If microorganisms are embedded, the drying may be performed by any of the methods set forth herein below. The particular method employed depends on the amount of residual moisture intended to be maintained in the bead, the condensation of the bead (higher temperatures produce more condensed beads), the nature and sensitivity of the active material and the size of the desired bead.

Drying can be performed by a method selected from: vacuum drying, freeze drying, spray drying, fluidized bed drying, oven drying, solar drying, infra-red drying and electrical drying. However, the higher the drying temperature, the higher the resultant density of the bead. If empty beads are prepared, the drying temperature is less critical, as there is no active agent therein.

Thus, the carrier bead structure may be influenced by composition, method of drying and the temperature used for drying. In order to change the dimensions and the bulk density of a preparation, a compression step may be included. Smaller beads can also be formed by drying mini-gels produced by electrical shearing.

Also, very small dried beads or carriers (in the range of single microns) can be prepared by drying of the gum solution in one step by spray drying. In this case, the shape is not necessarily spheroid, and may be irregular, as is the case following methods of size reduction.

As mentioned above, the present invention is further directed to a method of preparation of the above composition including an active agent being a drug, an agent used in the food industry and an agent used in agriculture. The active agent can be added to the hydrocolloid solution in step (A) or to the hydrocolloid/filler solution in step (B). It is also possible load the active agents through diffusion into the bead from the outside, by placing them in a media containing the desired active agent.

In another embodiment, where the active ingredient (drug or agent used in agriculture) is hydrophobic, the active agent can be included in a fatty material that is inserted into the bead by infusion (placing the beads in the media comprising the active material, preferably in a vacuum) and the fatty material comprising the active agent inside and/or on the bead is then allowed to solidify.

Another embodiment involves spraying sticky powder containing the active ingredient on the formed bead (or powder on a sticky surface), or trying to force it "as is" through the open pores of the bead under pressure.

In the hydrogel solution formation step, water, at least one polymer, and other materials are mixed together. In some cases, one or more active agents are added to the solution in this step. Typically, the ratio of the at least one polymer to the water is 0.5-20% (w/w). In some cases, the ratio is 1-3%, and in others 10-20%.

Water may be tap water, distilled water or deionized water, depending on the application. At least one polymer may be selected from, for example, but not limited to, agar, agarose, pectin, carrageenan, alginate, gellan, konjak mannan, xanthan gum and locust bean gum (LBG), or a combination thereof. Other gelling agents may be used, such as chitosan, starch, gelatin, curdlan and combinations thereof.

Additives may be added during this step. These additives may include one or more of an emulsifier, buffer, surfactant, a pH modifying agent, stabilizer and coloring agent, as are known in the art. For agricultural applications, additional or alternative additives may be added according to the particular application.

At least one active agent may be added during this step or during ensuing steps. The term "active agent" refers to an organic or inorganic compound, a biological material, or complex of compounds that affects the target, whether in vivo or in the environment in a desired manner. According to some embodiments, the active agent will be released from the beads comprising the inert filler in a slower release profile than would be obtained from the beads having the same composition without the inert filler. The carrier beads of the invention are therefore advantageous for active agents for which slow and/or controlled release is beneficial. By one embodiment, the active agent is a medicinally active agent, such as, but not limited to, a drug, a diagnostic agent or an imaging agent. The medicinally active agent may be any drug, pro-drug, combination of drugs, diagnostic agents, or imaging agents used in therapy or diagnosis.

Typically polymer(s), water and optional additive(s) are mixed by stirring under gentle heating (30-50° C.) to form a hydrogel solution. Agent(s) may be added to the solution under gentle heating or after cooling.

In a mixing step, at least one filler is mixed with the hydrogel solution. This may be by direct addition of the at least one filler to the hydrogel solution to form a preparative bead solution (in the form of a dispersion/suspension/emulsion). Alternatively, the filler may be mixed in water or another liquid to form a dispersion or suspension. In alternative embodiments, the filler may be finely dispersed, such as in an emulsion. Depending on the physical nature of preparative bead solution, the conditions for forming it will be varied from gentle stirring to high shearing for emulsion formation.

Non-limiting examples of fillers are talc, kaolin, calcium carbonate, silicon dioxide, titanium dioxide, alumina, powdered cellulose, microcrystalline cellulose, potassium cellulose material, and starch, e.g., potato or corn starch.

Normally, the filler has a mean particle size of 0.05-200 microns. More usually, the filler particle size is 0.1-100 microns. For certain embodiments, the filler material may be in the nanoparticle range.

In a bead forming step, the preparative bead solution is added to a gelling solution. The ratio of these solutions is typically such that the beads produced comprise 0.02 to 20% (w/w) of the hydrocolloid/polymer material, and more preferably 1 to 15% (w/w), and most preferably 1 to 3% (w/w), together with 10 to 15% (w/w) of filler material. The beads formed typically comprise 0-3% of active agent, selected from at least one of a medicinally active agent, (including a therapeutic agent, a diagnostic agent, an imaging agent and a prodrug), and an agriculturally active agent (including a chemical agent and a biological agent).

Gelling solution typically comprises bivalent cations such as $Ca^{++}$, $Fe^{++}$, $Sr^{++}$, $Pb^{++}$, $Ba^{++}$, or trivalent cations such as $Al^{+++}$. In some cases univalent ions such as $K^+$ may be used for gelling of kappa-carrageenan. There may be several sub-steps to this step. For example, salts containing the bi/tri-valent ions may be dissolved at a temperature range of 60-100° C. and the resultant solution may be cooled to 50° C. Thereafter, the bead preparative solution may be added to the resultant solution. Many alternatives to these sub-steps are construed to be within the scope of this invention. In this regard, see the below examples.

An alternative to cross-linking the polymer is to form the beads using hydrogen bonds which, in the case of agar or agarose, are produced spontaneously in the gelling process. Gelling solution may optionally comprise one or more additional gelling agents such as chitosan, starch, gelatin, curdlan and konjac mannan in the bead formation step. According to some embodiments, at least one active agent may be added at this stage.

Typically, in the hydropolymer bead preparative solution, the filler material comprises 10 to 15% (w/w) thereof (which translates to around 50 to 70% (w/w) of the dried weight of the bead).

The drugs used in the beads of the present invention may be drugs with an improved medicinal activity in a controlled-release profile relative to a free form. The drug may either be water soluble or insoluble. When a hydrophobic drug or water insoluble drug is used, the carrier beads may include a small quantity of oil and/or fat for solubilization of hydrophobic drug or an emulsion containing the same. It might be possible to emulsify the hydrophobic material within the gelling solution if an emulsifier is present. The bead may be tailored for carrying any possible drug or materials specified herein. The biological agents may include proteins, antibodies, peptides, nucleic acid based compounds and microorganisms which have a beneficial effect, such as probiotic bacteria.

In this bead formation step, the method of mixing preparative solution with the gelling solution will determine the wet bead size and the physical/chemical characteristics thereof. For example, if the solution is dropped into gelling solution, the size of the drops will largely determine the size of the wet beads formed therefrom.

It should be understood that, in certain examples, no active agent is added in any of steps and the beads thus formed will be empty beads. These beads may be used in medicine, agriculture or in environmental engineering to absorb poisons, toxins or other chemicals from a body, from the soil or from an aquatic or gaseous environment, respectively.

Typically, the beads of the present invention contain 0.02 to 20% (w/w) of the hydrocolloid/polymer material, and, more preferably, 1 to 15% (w/w), and, most preferably, 1 to 3% (w/w) of the wet bead. It should be noted that, while for most hydrocolloids 1-3% w/w of the bead is the preferable range, for gelatin the preferable range is 15-20% w/w.

In a bead drying step, wet beads are dried by either freeze-drying or vacuum-drying. Freeze-dried beads are obtained by storing wet beads (24 h) at –80° C. before freeze-drying (48 h) in a pilot-plant unit (Model 15 RSRC-X, Repp Industries Inc., Gardliner, N.Y.), operating at 33.3 Pa (150 mbar) and –45° C. Vacuum-dried beads are obtained by drying (48 h) in a vacuum-oven (VD 23/53/115, WTB Binder, Tuttlingen, Germany), operating at 35° C., 104 Pa. Moisture-content values (% WB) are calculated. To determine the moisture content in the beads, the dried beads (by freeze-drying or vacuum-drying) are further dried in a vacuum-oven for 24 h at 105° C., 104 Pa. Dried beads are formed using both of these alternative drying processes.

For some applications, the dried beads may be size-reduced in an optional size reduction step. For example, if dried beads have a mean size of 1-4 mm, they may be size reduced by milling, grinding, shearing or by other methods known in the art to reduce the bead size to small particles having a mean particle size of 20-80 microns.

Additionally or alternatively, to optimize the size reduction step, a compression step may be performed to increase the density of dry beads or particles. For example, the beads may be compressed using universal testing machine (UTM) #5544, with a deformation rate of 1 to 100 mm/min. The following examples are provided merely in order to illustrate some embodiments of the present invention and are to be construed in a non-limitative manner.

EXAMPLES

Examples 1A-3E

Bead Compositions

Examples 1A-1E

Beads were prepared with sodium alginate and 10% w/w of filler. In Example 1A, the filler was talc, in Example 1B, the filler was kaolin, in Example 1C, the filler was calcium carbonate, in Example 1D, the filler was potato starch and in Example 1E, the filler was corn starch (Table 1).

Sodium alginate powder, with a molecular mass of 60 to 70 kDa and containing 61% mannuronic acid and 39% guluronic acid (Sigma Chemical Co., St Louis, Mo.), was dissolved in double-distilled water at room temperature (3%, w/w) using a magnetic stirrer (Freed Electric, Haifa, Israel). Five different fillers (10%, w/w) were used: talc (Mw: 379.29, particle size: <5 µm) (Sigma), kaolin (Mw: 258.17, particle size: 0.1-4 µm) (Sigma), calcium carbonate (Mw: 100.09, particle size: 0.15-0.85 cm) (Merck, Darmstadt, Germany), potato starch (Mw: varies, particle size: 15-100 µm) (Sigma) and corn starch (Mw: varies, particle size: 5-25 µm) (Sigma).

In pharmaceutical science, fillers are used to increase the bulk volume and make up the desired size of the formulation and are required if the dose of the drug is low (15).

Alginate beads were produced, using the ionotropic method, by dropping the solution containing alginate and one of the five tested fillers dropwise into a $CaCl_2$ (Frutarom Ltd., Haifa, Israel) cross-linking solution (2%, w/w) (16).

The alginate beads were kept in the cross-linking solution for 24 h to ensure an equilibrium state. Then, the beads were washed with double-distilled water and dried to remove excess surface ions. Beads containing no filler were also produced and served as blanks.

Examples 2A-2E

Beads were prepared with agarose 3% w/w and 10% w/w of filler. In Example 2A, the filler was talc, in Example 2B, the filler was kaolin, in Example 2C, the filler was calcium carbonate, in Example 2D, the filler was potato starch and in Example 2E, the filler was corn starch (Table 1).

Agarose powder was dissolved in pre-heated double-distilled water (3%, w/w) at 90° C. After cooling the solution to 50° C., the different fillers (10%, w/w) were added.

In order to produce spherically shaped beads, the solution containing agarose and filler was dropped into double-distilled water through a paraffin oil layer (~5 mm) (Frutarom Ltd.).

Examples 3A-3E

Beads were prepared with sodium alginate and 10% w/w of filler. In Example 3A, the filler was talc, in Example 3B, the filler was kaolin, in Example 3C, the filler was calcium carbonate, in Example 3D, the filler was potato starch and in Example 3E, the filler was corn starch (Table 1).

Gelrite gellan gum powder (Sigma) was dissolved in pre-heated double-distilled water (2%, w/w) at 90° C. After cooling the solution to 50° C., the different fillers (10%, w/w) were added. Gellan beads were produced by dropping the solution containing gellan and filler into a $CaCl_2$ cross-linking solution (2%, w/w) through an oil layer.

The gellan beads were kept in the cross-linking solution for 24 h to ensure an equilibrium state. Then, the beads were washed with double-distilled water and dried to remove excess surface ions. Beads containing no filler were also produced and served as blanks.

Drug Loading

Beads for release purposes were produced according to the procedures detailed above, with diltiazem hydrochloride (Fluka Chemie A G, Buchs, Switzerland) being dissolved in the solution (2%, w/w) at 40° C. (room temperature for alginate beads) (FIG. 1).

In order to minimize drug losses, alginate and gellan beads were kept for 24 h in a cross-linking solution that contained an equal concentration of diltiazem hydrochloride, and the washing step with double-distilled water before drying was omitted. Beads for release purposes included (before drying): hydrocolloid (2% gellan/3% alginate/agarose, w/w), filler (10%, w/w), $CaCl_2$ (2%, w/w, alginate/gellan beads) and diltiazem hydrochloride (2%, w/w). The compositions of the different hydrocolloid carriers are summarized in Table 1.

TABLE 1

| | Composition of the hydrocolloid carriers* | | |
| --- | --- | --- | --- |
| | Hydrocolloid | | |
| | Alginate (3%, w/w) | Agarose (3%, w/w) | Gellan (2%, w/w) |
| | | Example No. | |
| Filler type* | Filler (10%, w/w) | Filler (10%, w/w) | Filler (10%, w/w) |
| Talc | 1A | 2A | 3A |
| Kaolin | 1B | 2B | 3B |
| Calcium carbonate | 1C | 2C | 3C |

TABLE 1-continued

Composition of the hydrocolloid carriers*

| | Hydrocolloid | | |
|---|---|---|---|
| | Alginate (3%, w/w) | Agarose (3%, w/w) | Gellan (2%, w/w) |
| | | Example No. | |
| Filler type* | Filler (10%, w/w) | Filler (10%, w/w) | Filler (10%, w/w) |
| Potato starch | 1D | 2D | 3D |
| Corn starch | 1E | 2E | 3E |
| Drug (2%, w/w) | Diltiazem hydrochloride | Diltiazem hydrochloride | Diltiazem hydrochloride |

*10% w/w of one filler was used in each example

Each formulation was dried by either freeze-drying or vacuum-drying.

Agricultural Uses

For agricultural purposes, instead of the active agent being a drug, a nitrogen fertilizer was included within the solution before drying. Nitrogen is essential for life processes in plants, and lack of nitrogen often limits plant growth. In general fertilizers such as calcium nitrate, calcium ammonium nitrate, ammonium nitrate, urea, urea ammonium nitrate solution, ammonium sulfate and anhydrous ammonia can be used. However, not every bead can support such systems. For example Ca-nitrogen fertilizer can be used as cross-linker and thus be included within the gel. It should also be noted that urea disrupts hydrogen bonds and therefore cannot be used in agar/agarose beads.

More information on nitrogen fertilizers can be found at the following website: www.ces.purdue.edu/extmedia/AY/AY-204.html.

Bead Drying

Examples 1A-3E

Beads were dried by either freeze-drying or vacuum-drying. Freeze-dried beads were obtained by storing wet beads (24 h) at −80° C. before freeze-drying (48 h) in a pilot-plant unit (Model 15 RSRC-X, Repp Industries Inc., Gardliner, N.Y.), operating at 33.3 Pa (150 mbar) and −45° C. Vacuum-dried beads were obtained by drying (48 h) in a vacuum-oven (VD 23/53/115, WTB Binder, Tuttlingen, Germany), operating at 35° C., 104 Pa. Moisture-content values (% WB) were calculated. To determine the moisture content in the beads, the dried beads (by freeze-drying or vacuum-drying) were further dried in a vacuum-oven for 24 h at 105° C., 104 Pa. The different drying methods were compared.

Estimation of Carrier Bead Diameter and Weight

Carrier bead diameter (±0.03 mm) was measured with a digital caliper (Mitutoyo, Tokyo, Japan). Carrier bead weight (±0.001 g) was measured with semi-micro balance 262SMA-FR SCS (Precisa Instruments, Bern, Switzerland). Carriers of each composition (five repetitions) were checked. Carriers of different compositions were photographed, before and after drying, using a digital camera (COOL-PIX5000, Nikon, Tokyo, Japan).

Example 4

Mechanical Testing

Compression Testing

Taking into account the mobility of the gastrointestinal tract, it is important to study the different mechanical properties of the carrier beads.

Compression tests were carried out to evaluate properties such as strength, fragility and toughness. Carriers of each composition of Examples 1A-3E (five duplicates) were compressed between lubricated parallel plates to a deformation of 90% at a constant deformation rate of 10 mm/min with an Instron Universal Testing Machine (UTM), Model 5544, connected to an IBM-compatible personal computer using a card.

Data acquisition and conversion of the Instron's continuous voltage vs. time output into digitized force vs. time relationships was performed by software ("Merlin") from Instron Corporation (Canton, Mass.). Finally, the force vs. time data was converted to stress vs. engineering strain relationships using the following equations:

$$\sigma = F/A_0 \quad (1)$$

$$\epsilon E = \Delta D/D_0 \quad (2)$$

wherein $\sigma$ is the stress (Pa), F is the force at a given time (N), $A_0$ is the initial cross-sectional area of the carrier $\epsilon E$ is the engineering strain (dimensionless), $\Delta D$ is the absolute deformation caused by the compression test (length units) and $D_0$ is the diameter of the carrier at time zero (length units).

Young's modulus was calculated from the initial linear portion of the stress vs. engineering strain curve. The Young's modulus value, i.e. the slope of the curve, is a parameter reflecting the toughness of the compressed carrier. Compression tests for the different carriers were carried out in five replicates. It should be noted that compression is possible mainly for "big" capsules (i.e in the size of at least one millimeter). For smaller beads/particles of a micron size range, different methods should be adopted.

Porosity Determination

Carriers of each composition (Examples 1A-3E) (five repetitions) were checked.

Carrier porosity was calculated using the following equation:

$$P = 1 - (\rho_b/\rho_s) \quad (4)$$

wherein P is the porosity value (dimensionless), $\rho_b$ is the bulk density (mass/volume) of the carrier bead and $\rho_s$ is the solid density (mass/volume) of the carrier bead. Bulk density was obtained from the ratio of mass to volume of the dried carrier. Solid density was evaluated by micro-pycnometer (Quantachrome, Syosset, N.Y.).

Reference is now made to FIG. 1, which shows electron microscope images of the outer surface of freeze dried agent carrier beads of Examples 1A-1E, in accordance with some embodiments of the present invention.

To study the structural changes within and on the surface of the carriers as a result of filler inclusion and drying, SEM micrographs were taken using a JEOL JSM 35C SEM (Tokyo, Japan). The carrier beads were attached to metal stubs and gold-coated (150-200 Å) in a Polaron 5150 sputter coater (Polaron Equipment Ltd., Holywall Industrial Estate Watford, Hertfordshire, England). Carriers of different compositions were checked.

It can be seen that the outer surface appeared smoother for Examples 1A-1E relative to the unfilled carrier bead Agarose, alginate and gellan carriers, with or without the inclusion of fillers, were designed for drug release. The weight of the dried carriers ranged between 9 and 17 mg. The diameters of the freeze-dried carriers ranged from 2.4 to 4.1 mm, whereas those of the vacuum-dried carriers ranged from 1.5 to 2.8 mm. With the freeze-drying method, the structural changes in the material were smallest (19), and therefore changes in their diameter during the drying process were smaller than those of their vacuum-dried counterparts. SEM micrographs of the outer surfaces of the carriers are revealing, since the dissolution medium penetrates the carrier's core via diffusion through its surface. All carriers were spheroids and their surface was quite smooth. Those that included kaolin or talc were less smooth, containing "bumps" on their outer surface area The diameters of these protrusions varied from a few microns to 0.2 and 0.3 mm for carriers filled with talc or kaolin, respectively.

Both kaolin and talc have the smallest particle diameters and due to their large number, they are distributed throughout the mass. Each distributed particle may serve as a "center" for crystallization, i.e. small bumps will form around these "centers".

Images of all carriers that contained no fillers showed surface "craters". These craters may have been a result of processing, i.e., freezing in the case of drying by freeze-dehydration. This was previously explained (20), taking into consideration the size of the filler itself (21-23). Addition of filler to the formulation contributed to a decrease in the number of the craters (see FIG. 1).

Figure 2:
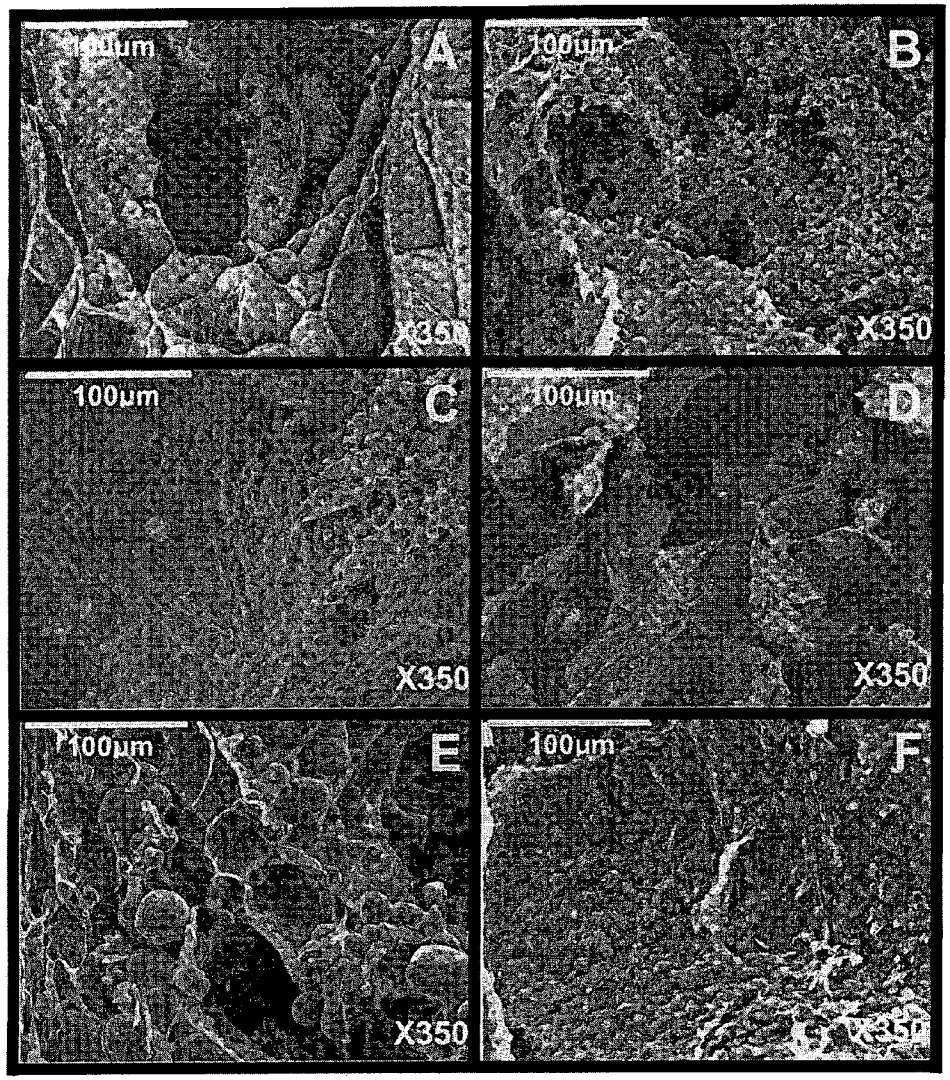
FIG. 2 shows electron microscope images of internal faces of inner surfaces of freeze-dried agent carrier beads, in accordance with some embodiments of the present invention.

FIG. 2 includes electron micrographs of different halved freeze-dried carrier beads. The size and distribution of the pores formed within the carriers are not homogeneous. However, the filler particles appear to occupy some of the distributed pores, as well as the cell carrier wall and surface. Whereas the interior of the spherical carriers (dried beads) was porous, their outer surface appeared quite smooth, with almost no structural "holes".

The porosity values of the freeze-dried carriers were significantly higher than those of their vacuum-dried counterparts: in the former, porosity values of freeze-dried carriers with filler inclusion ranged from 0.68 to 0.85 (porosity values of freeze-dried carriers without filler inclusion ranged from 0.9 to 0.95), whereas for in the latter they ranged from ~0.02 to 0.41 (porosity values of vacuum-dried carriers without filler inclusion ranged from 0.02 to 0.05).

Freeze-dried products are generally characterized by the least shrinkage and structural changes, and by the creation of pores in areas of former ice crystals (19).

Example 5

Bead Stability

Stability in Simulated Gastrointestinal Fluid

The stability of beads containing a fertilizer depends on the soil composition, soil temperature, its moisture content, wetting drying cycles, content of microorganisms within and their species and the proportion between different microorganism's content, etc. In general, the fertilizer diffuses out of the bead in a rapid manner in comparison to the decomposition of the dried bead.

The stages that a dried bead passes after its entrapment by soil granules, is wetting, sometimes swelling (not much), changes in color, diffusion of fertilizer followed by a slow disintegration. In the context of this example, slow means over a period of months. In water decomposition of 6 to 12 months is possible, however changes in the structure, color and texture occurs. Percent nitrogen in the dried bead could reach ~30 to 80%. Of course the smaller the amount of nitrogen compound the easier is the bead production.

Finally this information relies on unpublished experiments with ammonium sulfate and ammonium nitrate. Mechanism of dissolution and diffusion still needs some basic research. Also the upper limit of nitrogen content is an estimation, taking into consideration the increase in content by drying.

In order to evaluate the potential of the different carriers to serve as drug carriers, it was necessary to study their stability in solutions which mimic the gastro-intestinal fluids. The simulated gastrointestinal fluid was based on a previous report of Hack and Selenka (17) with some modifications. Simulated gastric fluid was prepared by dissolving 10 mg of pepsin from porcine stomach mucosa (Sigma) in 112 ml of double-distilled water, then adding 350 mg of mucine from porcine stomach (Sigma).

Thereafter, 3.5 ml of 3 N NaCl solution and 2 ml of 1.2 N KCl solution were added to the simulated gastric fluid. The pH value was adjusted and kept at pH 1.2 by adding an appropriate volume of 1 N HCl (Sigma). pH values (+0.03) were checked with an Extech Heavy Duty pH/mV Temperature Meter (Extech Instruments Co., Waltham, Mass.). A laboratory bottle (250 ml) filled with 120 ml of simulated gastric fluid was placed in a TEP-3 water bath (Freed Electric) using a magnetic stirrer (50 rpm). The bath, filled with pre-heated water (37±0.5° C.), was controlled by an electric heating element.

Carrier beads of different compositions were immersed in this simulated gastric fluid for 3 h. The volume of the simulated gastrointestinal fluid was 200-fold higher than that of the immersed carriers. Thereafter, the simulated gastric fluid was titrated by adding an appropriate amount of sodium bicarbonate (Frutarom Ltd.).

The pH value was adjusted and kept at pH 6.8. Trypsin (10 mg) from porcine pancreas (Sigma), 350 mg of pancreatin from porcine pancreas (Sigma) and 350 mg of dried bovine bile (Sigma) were added to obtain simulated intestinal fluid. Carriers were immersed in the simulated intestinal fluid for 6 h (17). Thus, the immersion was performed in two stages, with immersion in the simulated gastric fluid being followed by immersion in the simulated intestinal fluid. Time of immersion of the different carriers in the simulated fluids was in accordance with the model developed by Hack and Selenka (17) and with the literature referring to the passage time of solids through the stomach and small intestine (17, 18). Three replicates were used for each formulation. It should be noted that at this stage, the carriers do not contain any actual drugs. After each stage, the carriers were photographed using a digital camera, and their diameters and weights were checked in accordance to that which has been described previously. The experiment was carried out in three repetitions.

TABLE 2

Stability of the carriers in simulated gastro-intestinal fluid*

| Composition | Time 0 | | Gastric juice (2 h) | | Intestinal juice (6 h) | |
|---|---|---|---|---|---|---|
| | Weight (mg) | Diameter (mm) | Weight change (%) | Diameter change (%) | Weight change (%) | Diameter change (%) |
| 3% Alginate - Freeze Drying | 2.8 ± 1.0 | 2.56 ± 0.04 | 128.6 ± 2.6 | 12.3 ± 1.3 | 455.7 ± 32.6 | 67.2 ± 3.2 |
| 3% Alginate - Vacuum Drying | 2.9 ± 0.0 | 1.73 ± 0.01 | 75.5 ± 19.5 | 17.9 ± 1.2 | 376.6 ± 20.1 | 125.6 ± 12.7 |
| 3% Alginate + 10% Talc - Freeze Drying | 14.9 ± 1.3 | 3.65 ± 0.07 | 63.3 ± 2.9 | 6.7 ± 3.6 | 649.5 ± 39.4 | 69.9 ± 1.7 |
| 3% Alginate + 10% Talc - Vacuum Drying | 14.8 ± 0.7 | 2.73 ± 0.04 | 53.0 ± 1.1 | 11.4 ± 1.4 | 360.5 ± 1.5 | 83.1 ± 6.4 |
| 3% Alginate + 10% Calcium carbonate - Freeze Drying | 12.2 ± 1.1 | 3.05 ± 0.00 | 23.5 ± 0.3 | 12.0 ± 0.2 | 333.3 ± 43.2 | 58.0 ± 0.5 |
| 3% Alginate + 10% Calcium carbonate - Vacuum Drying | 13.0 ± 0.6 | 2.55 ± 0.00 | 18.2 ± 2.5 | 6.1 ± 1.4 | 366.8 ± 0.6 | 85.3 ± 2.5 |
| 3% Alginate + 10% Potato starch - Freeze Drying | 12.8 ± 0.3 | 3.83 ± 0.04 | 143.8 ± 20.9 | 12.7 ± 0.1 | 725.0 ± 28.2 | 45.6 ± 0.6 |
| 3% Alginate + 10% Potato starch - Vacuum Drying | 13.9 ± 0.2 | 2.55 ± 0.07 | 60.8 ± 5.2 | 25.1 ± 1.3 | 418.0 ± 43.7 | 74.0 ± 2.9 |
| 3% Agarose - Freeze Drying | 2.5 ± 0.4 | 3.22 ± 0.09 | 122.7 ± 9.6 | 15.7 ± 3.8 | 156.2 ± 15.4 | 17.9 ± 0.5 |
| 3% Agarose - Vacuum Drying | 2.9 ± 0.4 | 1.81 ± 0.06 | 185.4 ± 14.9 | 26.5 ± 2.6 | 228.6 ± 5.3 | 34.5 ± 2.7 |
| 3% Agarose + 10% Talc - Freeze drying | 15.5 ± 0.4 | 3.67 ± 0.02 | 128.1 ± 5.8 | 6.7 ± 1.0 | 156.8 ± 18.0 | 15.1 ± 1.4 |
| 3% Agarose + 10% Talc - Vacuum Drying | 13.0 ± 0.3 | 2.53 ± 0.11 | 71.9 ± 4.9 | 22.0 ± 1.2 | 82.7 ± 21.5 | 24.8 ± 2.4 |
| 3% Agarose + 10% Calcium carbonate - Freeze Drying | 11.3 ± 1.8 | 3.80 ± 0.07 | 243.1 ± 49.5 | 15.0 ± 1.4 | 248.4 ± 47.8 | 15.8 ± 0.3 |
| 3% Agarose + 10% Calcium carbonate - Vacuum Drying | 14.3 ± 0.4 | 2.70 ± 0.07 | 77.5 ± 0.6 | 21.9 ± 2.1 | 89.1 ± 3.7 | 25.0 ± 0.7 |
| 3% Agarose + 10% Potato starch - Freeze Drying | 8.3 ± 0.6 | 3.80 ± 0.07 | 364.5 ± 20.6 | 18.0 ± 0.9 | 373.5 ± 25.5 | 18.4 ± 0.7 |
| 3% Agarose + 10% Potato starch - Vacuum Drying | 14.9 ± 1.3 | 2.70 ± 0.07 | 116.2 ± 18.7 | 35.7 ± 2.3 | 121.2 ± 14.8 | 36.5 ± 3.5 |
| 2% Gellan - Freeze Drying | 2.8 ± 0.0 | 2.96 ± 0.00 | 85.4 ± 4.6 | 19.3 ± 0.4 | 325.2 ± 16.3 | 27.1 ± 0.2 |
| 2% Gellan - Vacuum Drying | 2.9 ± 0.2 | 1.41 ± 0.00 | 111.3 ± 13.3 | 34.2 ± 6.6 | 334.48 ± 13.2 | 69.6 ± 3.3 |
| 2% Gellan + 10% Talc - Freeze Drying | 10.1 ± 0.1 | 3.55 ± 0.00 | 56.2 ± 2.5 | 3.4 ± 0.4 | 89.6 ± 9.1 | 4.1 ± 0.2 |
| 2% Gellan + 10% Talc - Vacuum Drying | 13.4 ± 0.1 | 2.48 ± 0.01 | 31.7 ± 4.0 | 14.8 ± 0.9 | 52.6 ± 2.1 | 18.8 ± 0.9 |
| 2% Gellan + 10% Calcium carbonate - Freeze Drying | 12.6 ± 0.6 | 3.47 ± 0.08 | 21.1 ± 2.9 | 7.7 ± 0.9 | 49.6 ± 1.2 | 12.3 ± 0.1 |
| 2% Gellan + 10% Calcium carbonate - Vacuum Drying | 12.4 ± 0.5 | 2.62 ± 0.03 | 13.0 ± 2.9 | 6.7 ± 0.2 | 51.1 ± 0.8 | 7.8 ± 0.7 |

TABLE 2-continued

Stability of the carriers in simulated gastro-intestinal fluid*

| | Time 0 | | Gastric juice (2 h) | | Intestinal juice (6 h) | |
|---|---|---|---|---|---|---|
| Composition | Weight (mg) | Diameter (mm) | Weight change (%) | Diameter change (%) | Weight change (%) | Diameter change (%) |
| 2% Gellan + 10% Potato starch - Freeze Drying | 12.0 ± 0.1 | 3.94 ± 0.00 | 186.6 ± 3.6 | 10.3 ± 0.2 | 259.0 ± 5.7 | 15.4 ± 0.2 |
| 2% Gellan + 10% Potato starch - Vacuum Drying | 13.3 ± 0.6 | 2.62 ± 0.00 | 77.1 ± 16.6 | 29.4 ± 0.6 | 142.9 ± 0.3 | 42.8 ± 1.9 |

*Data shown are the mean ± SD of three replicates.

Example 6

Bead Dissolution

In-Vitro Dissolution and Drug-Release Studies

In-vitro dissolution and drug-release studies were performed at 37±0.5° C. using a TEP-3 water bath. A laboratory bottle (1000 ml) containing 900 ml of water as the dissolution medium was placed in the water bath, and the medium was stirred by magnetic stirrer (50 rpm). The pH value was adjusted and kept at 1.2 by adding an appropriate volume of 1 N HCl solution. After 2 h, the pH of the dissolution medium was adjusted and kept at pH 6.8 by adding an appropriate amount of sodium bicarbonate. Alginate-based carriers containing diltiazem hydrochloride were used in all drug-release studies.

At scheduled times, 3-ml samples were withdrawn for spectrophotometric determination and replaced by equivalent volumes of fresh dissolution medium. The amount of drug released at a given time was determined with a UV-1601 UV-VIS spectrophotometer (Shimadzu, Kyoto, Japan) at 237 nm. During the course of the experiments, the carriers were photographed using a digital camera. Prior to the studies, a standard curve was plotted.

Statistical Analysis

Statistical analyses were conducted using JMP software (SAS Institute, 1995), including ANOVA and the Tukey-Kramer Honestly Significant Difference test for comparisons of means. $P \leq 0.05$ was considered significant.

Sucrose Release

Beads were prepared as described above with and without different fillers (at amounts of 5% or 10%) with the active ingredient released being sucrose. The amount of sucrose in 1 gram of beads was 0.45 gram.

The release was tested by placing one gram beads into 4 grams of distilled water.

The release rates were checked after an hour and it was found that release from beads without filler was 0.45 gram sucrose. Beads having 5% filler ($SiO_2$ Kaolin, Talc, $CaCO_3$, Bentonite) released about 0.24-0.32 sucrose in the same time period; and beads having 10% filler ($SiO_2$, Kaolin, Talc, $CaCO_3$) release 0.16-0.24 gram sucrose. As evident the higher the filler value the lower the amount of sucrose released.

Although the above results are for a time of 1 hour after placing the beads in the water the test was done again after 6 hours and the asymptotic value has not changed.

The asymptotic release rate was highest for beads without a filler, than for beads with 5% filler and lowest for beads with 10% filler.

Of the fillers tested, those with talc showed the slowest release rate and those with $SiO_2$ the highest release rates.

To summarize: the higher the filler percentage in the beads the lower the total amount of sucrose released as well as the lower release rate.

Further discussion of the release trends are discussed hereinbelow with respect to FIGS. 7-8.

Figure 3:
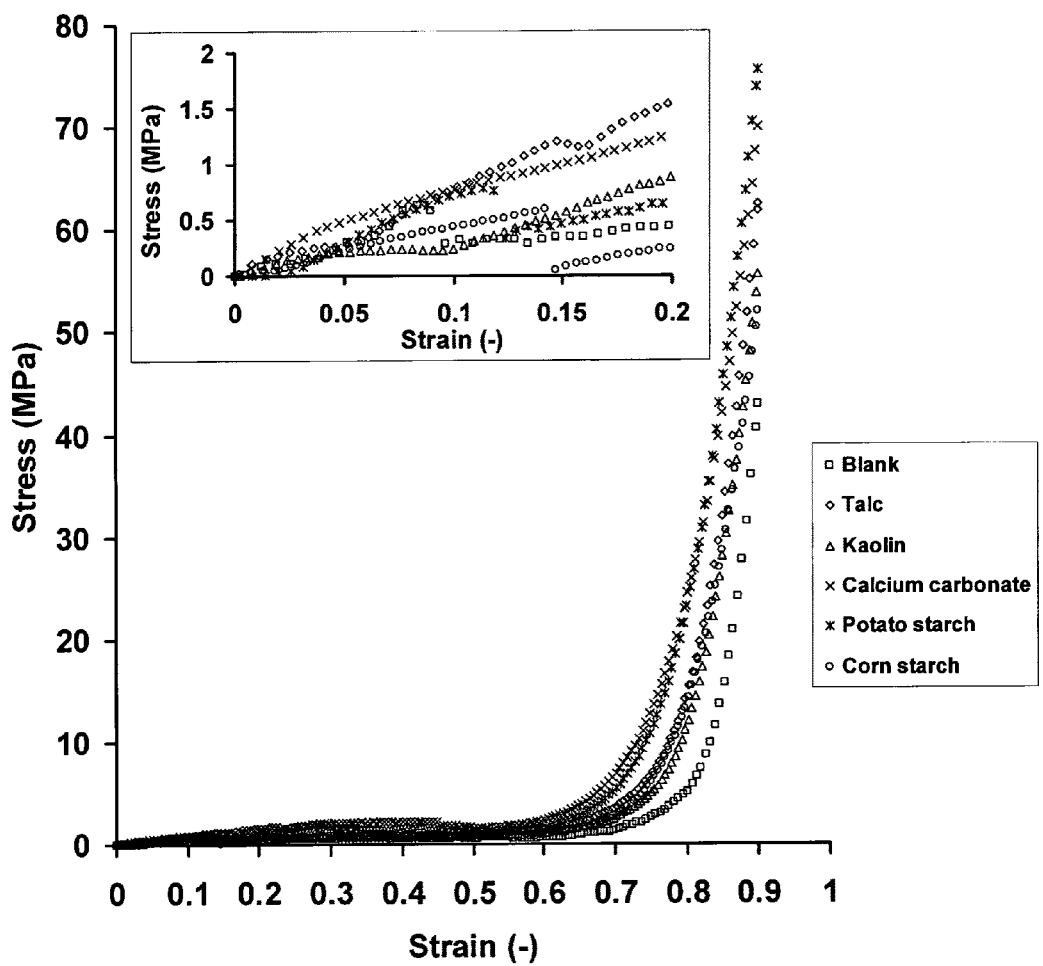
FIG. 3 is a graph of typical stress-strain relationships for freeze-dried alginate agent carrier beads with and without fillers (data shown are the mean of five replicates), in accordance with an embodiment of the present invention.

Reference is now made to FIG. 3, which is a graph of typical stress-strain relationships for freeze-dried alginate agent carrier beads with and without fillers (data shown are the mean of five replicates), in accordance with an embodiment of the present invention.

The mechanical properties of the different carriers were evaluated by compression test. FIG. 3 represents stress-strain relationships for freeze-dried alginate carriers with and without fillers. The inset picture demonstrates that up to a strain of ~0.2, an approximately linear stress-strain relationship exists, and the Young's modulus can therefore be easily calculated.

Figure 4:
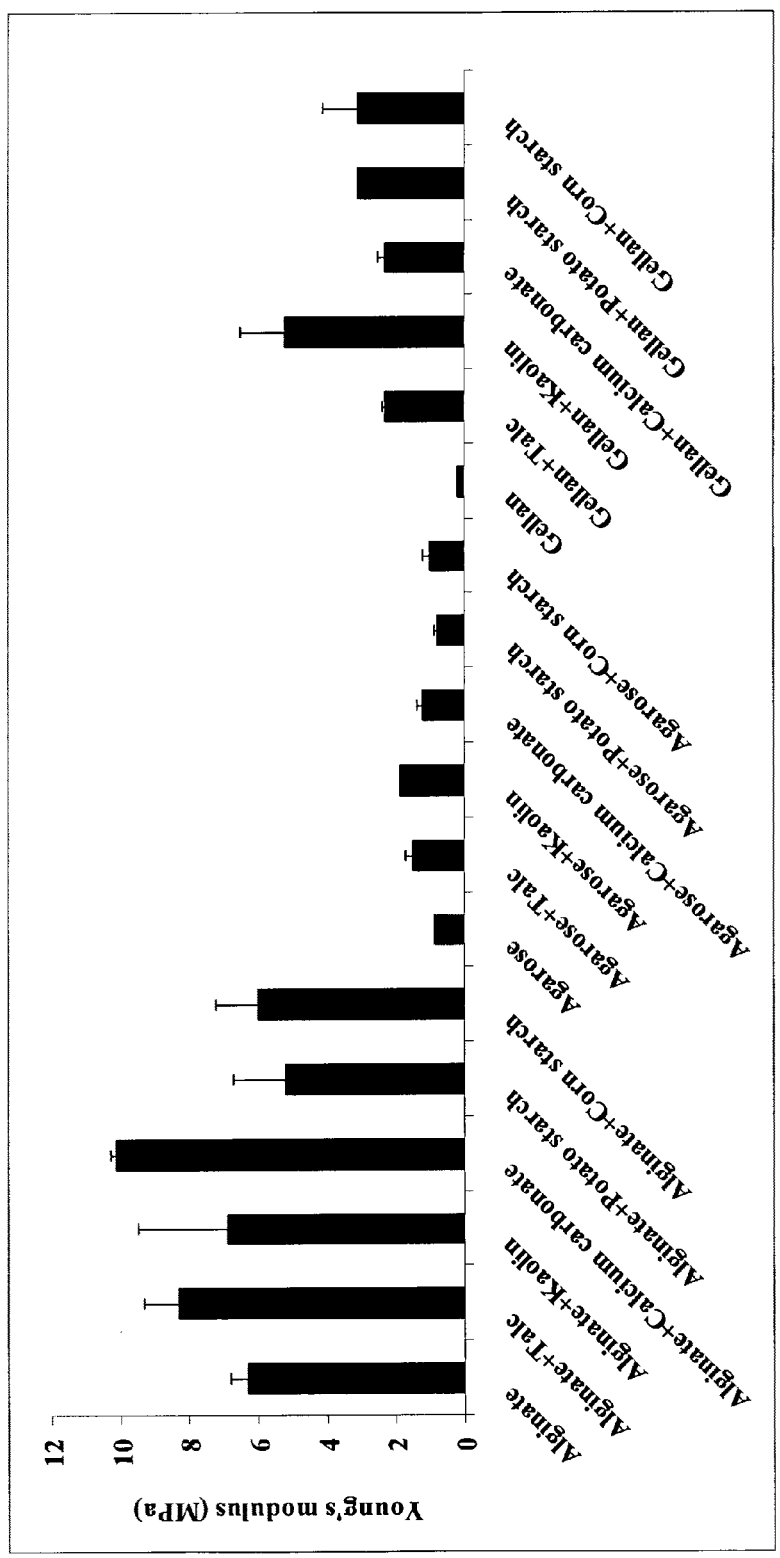
FIG. 4 is a graph of values of Young's modulus of freeze-dried agent carrier beads (data shown are the mean±SD of five replicates), in accordance with an embodiment of the present invention.

FIG. 4 is a graph of values of Young's modulus of freeze-dried agent carrier beads (data shown are the mean±SD of five replicates), in accordance with an embodiment of the present invention.

The Young's modulus values of freeze-dried carrier beads are summarized in FIG. 4. $R^2$ values ranged from 0.8777 to 0.9980. The alginate-calcium carbonate carriers were the toughest (had the highest Young's modulus value), being slightly higher than that of alginate-talc carrier beads. In contrast, the alginate carrier beads including potato starch were the least tough (had the lowest Young's modulus value).

The agarose-containing beads were 3-5 times tougher than the corresponding agarose beads and 1-3 times tougher than the corresponding gellan beads.

Figure 5:
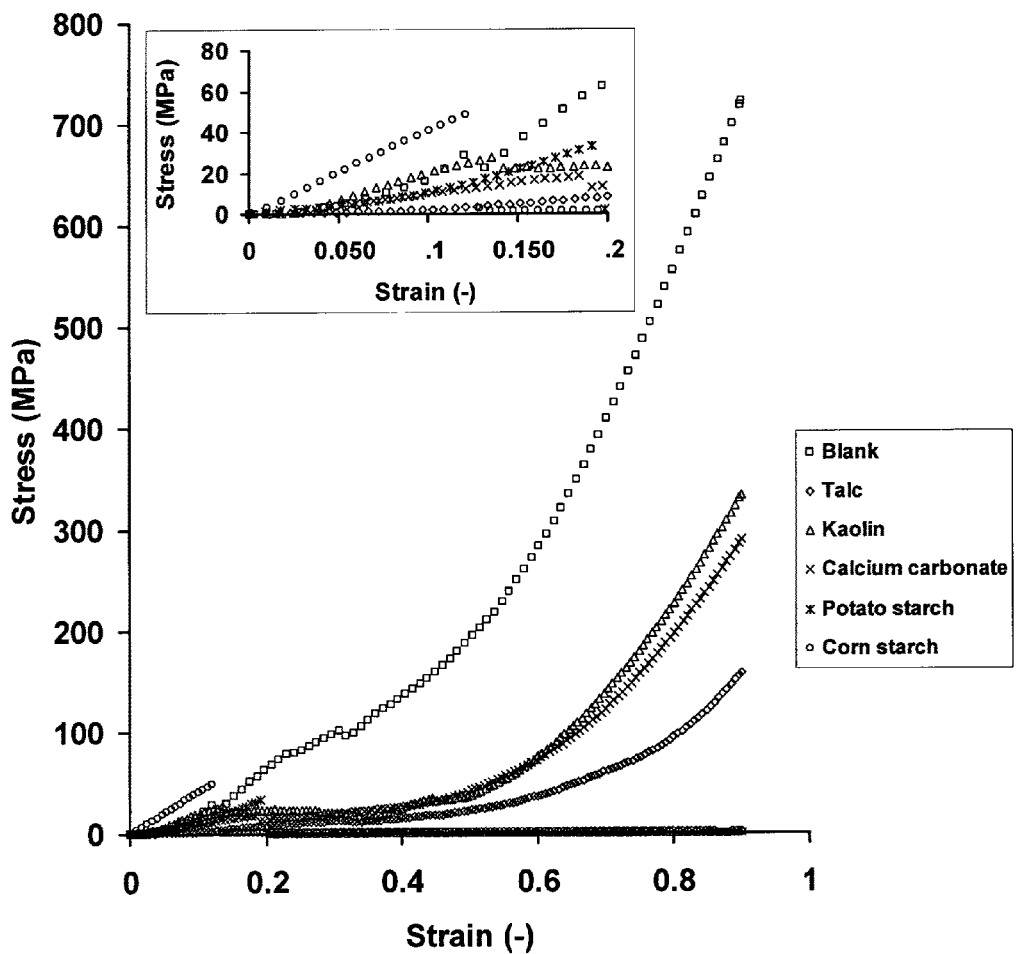
FIG. 5 is a graph of typical stress-strain relationships for vacuum-dried alginate carrier beads with and without fillers (data shown are the mean of five replicates), in accordance with an embodiment of the present invention.

FIG. 5 is a graph of typical stress-strain relationships for vacuum-dried alginate carrier beads with and without fillers (Data shown are the mean of five replicates), in accordance with an embodiment of the present invention;

FIG. 5 represents stress-strain relationships for vacuum-dried alginate carrier beads with and without fillers. Carrier beads filled with potato or corn starch were very strong, but also brittle, in comparison to the others. Vacuum-dried beads based on agarose or gellan filled with potato or corn starch were also strong, but brittle (data not shown). These results could be the outcome of the more considerable collapse of the gel matrix in vacuum- versus freeze-drying. The Young's modulus values of vacuum-dried carriers are summarized in FIG. 6.

Figure 6:
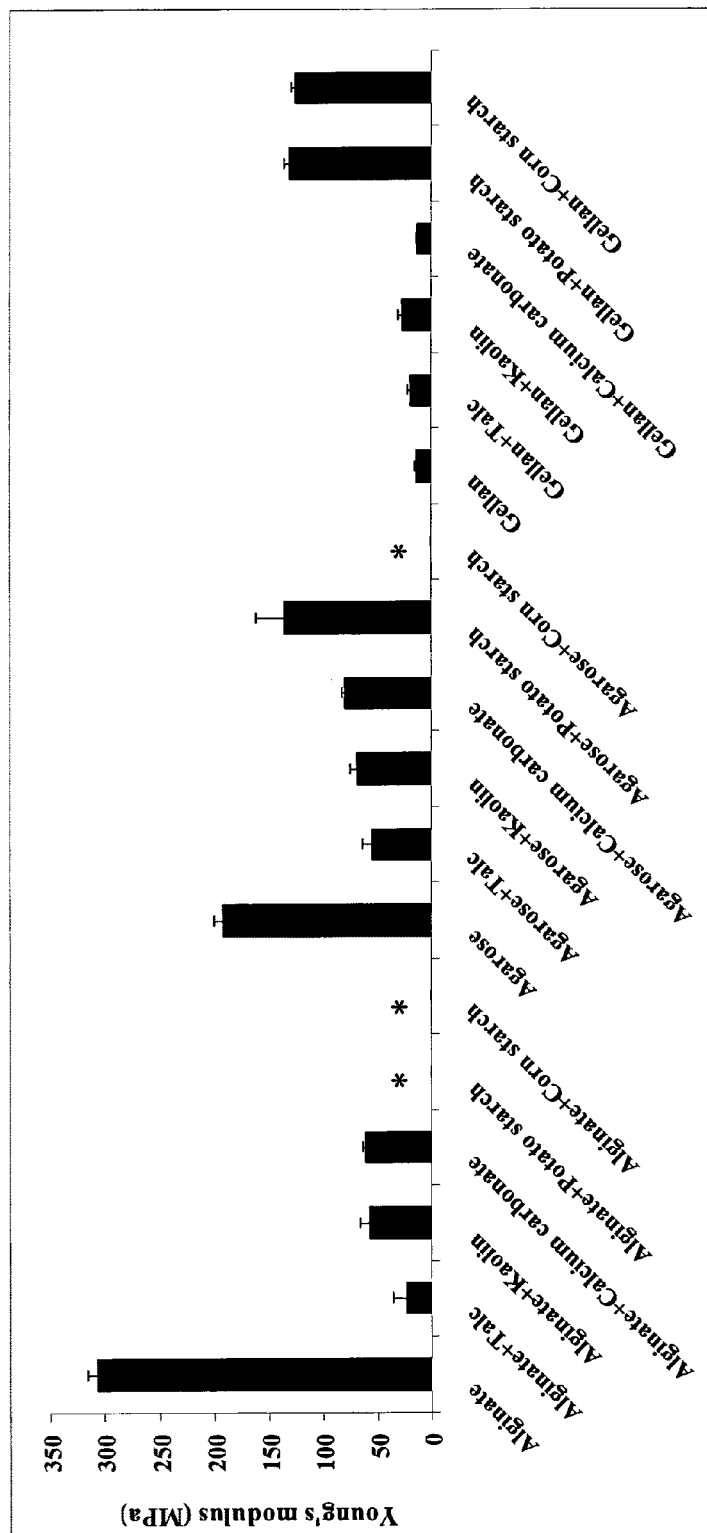
FIG. 6 is a graph of values of Young's modulus of vacuum-dried carriers (data shown are the mean±SD of five replicates), in accordance with an embodiment of the present invention; * indicates that beads exploded during the testing.

FIG. 6 is a graph of values of Young's modulus of vacuum-dried carriers (data shown are the mean±SD of five replicates), in accordance with an embodiment of the present invention. $R^2$ values ranged from 0.8342 to 0.9885. To compare the mechanical properties of the different carrier-filler moieties, we evaluated stress at the pre-determined strain values of 0.3, 0.6 and 0.9. These strain values were chosen to divide the strain range into three equal regions. Moreover, comparing the adjacent stress values could then demonstrate when a cellular solid has a greater resistance to deformation.

In general, the freeze-dried carriers were weaker than those dried by vacuum. For example, the freeze-dried 3% alginate-based carrier had a stress value of 42.9 MPa at a strain of 0.9, versus 721.2 MPa for its vacuum-dried counterpart (data not shown).

Carriers produced from alginate, regardless of whether they were freeze- or vacuum-dried, were stronger than those based on agarose or gellan, the latter being the weakest.

Generally, the linear shape of the stress-strain relationships with alginate also existed for agarose- and gellan-based carriers (data not shown). Drug inclusion contributed to weakening of the carrier due to interference with the gellification process.

Alginate (no filler added) beads undergo considerable shrinkage, and therefore after drying, these hydrocolloid beads had shrunk a bit more than those composed of agarose or gellan.

The carrier beads were examined in simulated gastrointestinal fluid in order to estimate their potential as drug carriers, prior to the dissolution tests. Some modifications were carried out in the gastrointestinal model previously suggested by Hack and Selenka (17).

The pH values of the simulated gastric and intestinal fluids were adjusted to, and maintained at pH 1.2 (3 h) and 6.8, respectively. A KCl solution was added in order to simulate physiological concentrations of potassium ions. Whole milk powder was not used in this study.

Changes in carrier diameter and weight during their immersion in the simulated gastro-intestinal fluid are summarized in Table 2. Note that the changes are given as percent change (increase) relative to initial values. In general, after their immersion in the simulated gastric or intestinal fluids, freeze-dried carriers absorbed larger amounts of fluid than their vacuum-dried counterparts, but did not necessarily swell more (as reflected by percent change in weight and/or diameter). This was due to the fact that the initial dimensions of the freeze-dried carriers were significantly larger than those of their vacuum-dried counterparts.

The explanation for this finding relates to the significant differences between the porosity values of the freeze-dried vs. vacuum-dried carriers. Generally, during rehydration, porous products can absorb larger amounts of water (19). Thus, in the gastrointestinal tract, the porosity of the carrier may affect the rate of fluid penetration into it. All of the examined carriers stabilized after immersion in the gastro-intestinal fluid. The simulated gastrointestinal fluid contained the following enzymes: pepsin and trypsin, which cleave proteins, α-amylase which cleaves starch, and pancreatin which contains amylase and lipase.

Alginate, agarose and gellan were all resistant to enzymatic cleavage by the enzymes tested. Of all fillers used in this study, only potato and corn starch were sensitive to enzymatic cleavage, by α-amylase. Nevertheless, during the 6-h immersion in the simulated intestinal fluid, carriers that contained starch remained intact.

The pH value of the dissolution medium was adjusted and kept at pH 1.2, while after 2 h the pH value was adjusted and kept at pH 6.8 till complete release of the drug from the carriers immersed in. The drug-release studies were not carried out in the gastrointestinal fluid, because the contents of enzymes and other solutes made the spectrophotometric determinations difficult to perform. Therefore, the dissolution media included no additives, except for HCl solution and sodium bicarbonate salt.

Dissolution studies revealed different disintegration processes for the freeze- and vacuum-dried carriers during their immersion in the dissolution mediums. Under acidic conditions (pH 1.2), no disintegration was observed. After a short period of time at pH 6.8, the carriers began to swell. As expected, the freeze-dried carriers absorbed more dissolution medium (absolute weight).

Figure 7:
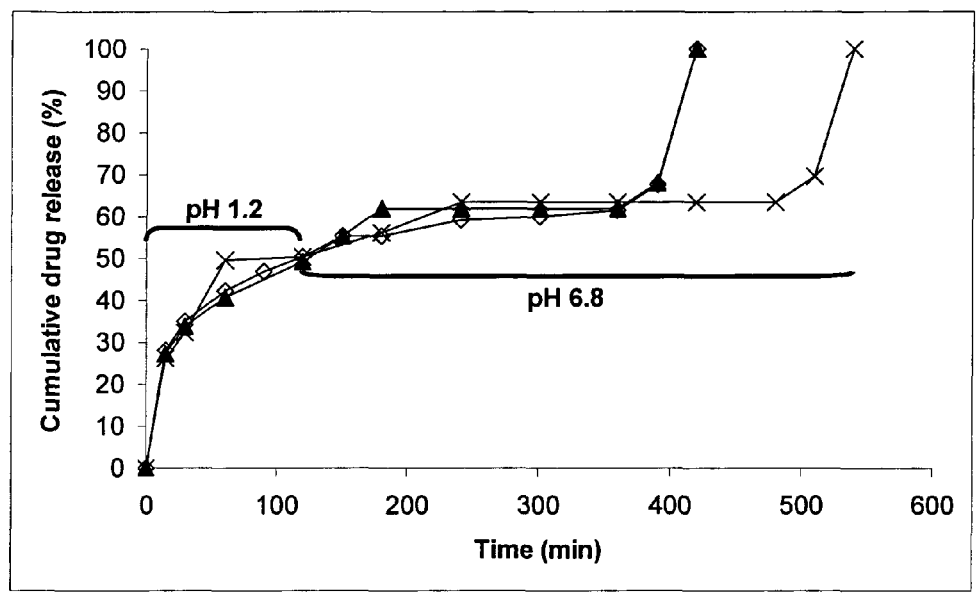
FIG. 7 is a graph of three in-vitro release profiles: freeze-dried talc alginate (◊); freeze-dried potato starch-alginate (x); freeze-dried corn starch-alginate (▲), in accordance with an embodiment of the present invention.
Figure 8:
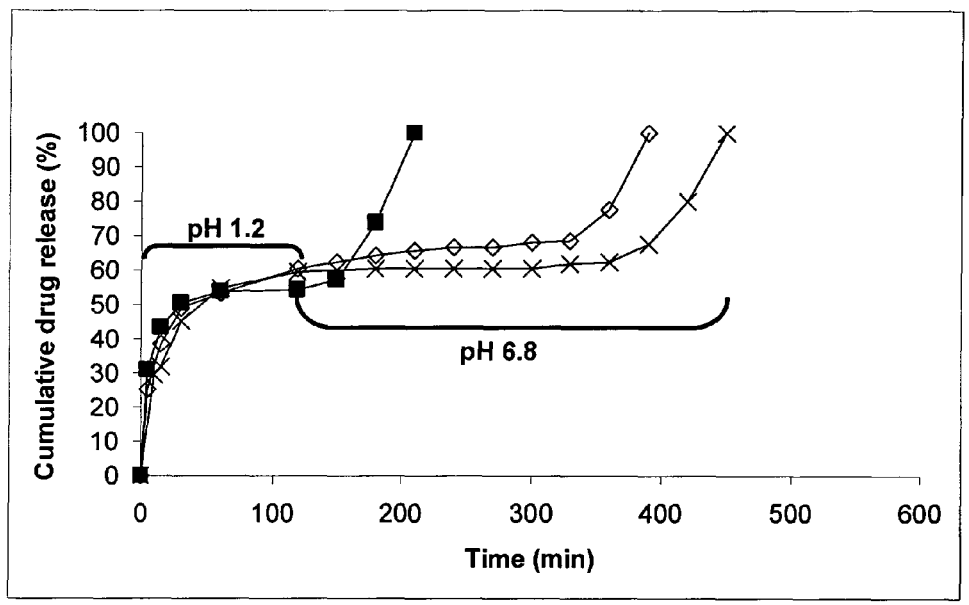
FIG. 8 is a graph of three additional in-vitro release profiles: vacuum-dried alginate (■); vacuum-dried talc-alginate (◊); vacuum-dried potato starch-alginate (x), in accordance with an embodiment of the present invention.

Reference is now made to FIGS. 7-8. FIG. 7 is a graph of in-vitro release profiles: freeze-dried talc alginate (◇); freeze-dried potato starch-alginate (x); freeze-dried corn starch-alginate (▲)), in accordance with an embodiment of the present invention. FIG. 8 is a graph of in-vitro release profiles: vacuum-dried alginate (■); vacuum-dried talc-alginate (◇); vacuum-dried potato starch-alginate (x), in accordance with an embodiment of the present invention.

FIGS. 7 and 8 show the release profiles of diltiazem hydrochloride from different carriers during immersion in the dissolution media. As already noted, in the acidic solution, no disintegration was observed, and about 40 to 50% of the drug was released over a period of ~2 h. The rapid drug release at the beginning of the dissolution test was related to the "burst effect". Factors affecting this phenomenon are amount of drug on the outer surface of the carrier and the high solubility of diltiazem hydrochloride in water.

At pH 6.8, the disintegration process resulted in completion of the release. Freeze-dried carriers absorbed dissolution medium until their complete disintegration. When the carriers began to disintegrate more than 30% of the loaded drug still remained within them. For freeze-dried carriers that contained talc, potato starch or corn starch, 70% of the drug was released after 390, 510 and 390 min, respectively. Freeze-dried alginate carriers that contained potato starch could absorb large amounts of dissolution medium (as well as large amounts of simulated fluids, as indicated in Table 2) and therefore began disintegrating at a later time point relative to freeze-dried alginate carriers containing any other filler.

Drug release from freeze-dried alginate carriers with no filler was not tested, because those carriers were deformed and amorphous, and only limited success was achieved with the drug loading. The disintegration process of vacuum-dried carriers included swelling, followed by continuous disintegration. The release profiles of the vacuum-dried alginate carriers with and without fillers were the same at pH 1.2. However, at pH 6.8, the carriers with no filler disintegrated much faster than the filler-containing vacuum-dried alginate carriers. Moreover, drug release from carriers that contained no filler was significantly faster than that from carriers with filler. For vacuum-dried carriers that contained talc or potato starch, 70% of the drug was released after 330 and 390 min, respectively.

In contrast, in vacuum-dried carriers containing no filler, 70% of the drug was released after only 180 min. However, similar release profiles were observed for the carriers containing different fillers. Thus, filler inclusion, but not the type of filler, contributes to the stability of the carriers in dissolution medium, and prolongs the overall time of drug release.

Without wishing to be bound by any theory, it is possible that the filler particles served as "physical barriers", thereby slowing the diffusion of the drug from the carriers.

It may thus be concluded that hydrocolloids such as agarose, alginate and gellan are suitable for the easy preparation of drug carriers, agricultural fertilizers, vitamins, minerals, pigments and microorganisms for slow-release purposes. The inclusion of fillers contributed to the stability and mechanical properties of the carriers. These carriers were spheroids with smooth or rugged surfaces. Their disintegration times and drug release were longer than with comparison to carriers that did not include fillers. The parameters influencing the characteristics of the disintegration and drug release were porosity, filler inclusion and drying method. Although capsules were created by different procedures and included different compositions, the complete drug release times were very similar, demonstrating a limited range for such moieties and indicating that, if further changes are needed, then other techniques, such as coating and inclusion of other structural modifiers, need to be applied.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

REFERENCES

1. El-Kamel A H, Al-Gohary O M N, Hosny E A. 2003. Alginate-diltiazem hydrochloride beads: optimization of formulation factors, in-vitro and in-vivo availability. J Microencapsul 20(2):221-225.
2. Liu P, Krishnan T R. 1999. Alginate-pectin-poly-L-lysine particulate as a potential controlled release formulation. J Pharm Pharmacol 51(2):141-149.
3. Hwang S J, Rhee G J, Lee K M, Oh K H, Kim C K. 1995. Release characteristics of ibuprofen from excipient-loaded alginate gel beads. Int J Pharm 116(1):125-128.
4. Panchgnula R, Thomas N S. 2000. Biopharmaceutics and pharmacokinetics in drug research. Int. J, Pharm 201(2): 131-150.
5. Leopold C S. Coated dosage forms for colon-specific drug delivery. 1999. PSTT 2(5):197-204.
6. Ferreira Almeida P, Almeida A J. 2004. Cross-linked alginate-gelatin beads: a new matrix for controlled release of pindolol. J Controlled Release 97(3):431-439.
7. Tapia C, Escobar Z, Costa E, Sapag-Hagar J, Valenzuela F, Basualto C, Gai M N, Yazdani-Pedram M. 2004. Comparative studies on polyelectrolyte complexes and mixtures of chitosan-alginate and chitosan-carrageenan as prolonged diltiazem chlorhydrate release systems. Eur J Pharm Biopharm 57(1):65-75.
8. Toti U S, Aminabhavi T M. 2004. Modified guar gum matrix for controlled release of diltiazem hydrochloride. J Controlled Release 95(3):567-577.
9. Kedzierewicz F, Lombry C, Rios R, Hoffman M, Maincent P. 1999. Effect of the formulation in-vitro release of propranolol from gellan beads. Int J Pharm 178(1):129-136.
10. Haglund B O, Upadrashta S M, Neau S H, Cutrera M A. 1994. Dissolution controlled drug-release from agarose beads. Drug Dev Ind Pharm 20(6):947-959.
11. Nussinovitch A. 1997. Hydrocolloid applications: Gum technology in the food and other industries, 1st ed., London, UK: Chapman and Hall.
12. Homsy W, Lefebvre M, Caille G, Du Souich Patrick. 1995. Metabolism of diltiazem in hepatic and extrahepatic tissues of rabbits: in-vitro studies. Pharm. Res 12(4):609-614.
13. Buckley M M T, Grant S M, Goa K L, McTavish D, Sorkin E M. Diltiazem—A reappraisal of its pharmacological and therapeutic use. Drugs 39(5):757-806.
14. Katzung B G. 2004. Basic & clinical pharmacology, 9th ed., New York: McGraw-Hill/Appleton & Lange. p. 160-240.
15. Aulton M E. 2002. Pharmaceutics: The science of dosage form design, 2nd ed., New York: Churchill Livingstone. p. 404-405.
16. Nussinovitch A, Peleg M, Mey-Tal E. 1996. Apparatus for the continuous monitoring of changes in shrinking gels. Food Hydrocolloids 10(2):137-141.
17. Hack A, Selenka F. 1996. Mobilization of PAH and PCB from contaminated soil using a digestive tract model. Toxicol Lett 88(1-3):199-210.
18. Washington N, Washington C, Wilson C G. 2003. Physiological pharmaceutics: Barriers to drug absorption, 2nd ed., New York: Taylor & Francis. p. 85-101, 124-125.
19. Fennema O R. 1975. Principles of food science, Part II: Physical principles of food preservation, New York: Marcel Dekker, Inc.
20. Zohar-Perez C, Chet I, Nussinovitch A. 2004. Irregular surface-textural features of dried alginate-filler beads. Food Hydrocolloids 18(2):249-258.
21. Dixon J B, Weed S B. 1989. Minerals in soil environments, 2nd ed., Madison, Wis.: Soil Science Society of America.
22. Budaravi S, O'Neill M J, Smith A, Heckelman P E, Kinneary J F. 1996. The Merck index: An encyclopedia of chemicals, drugs, and biologicals, 12th ed., Whitehouse Station, N.J.: Merck and Co., Inc.
23. Grim, R E. 1968. Clay mineralogy, 2nd ed., New York: McGraw-Hill.
24. Zohar-Perez, C, Chernin, I. C and Nussinovitch, 2003 A. Structure of dried cellular alginate matrix containing fillers provides extra protection for microorganisms against UVC radiation. Radiation Research 160, 198-204.
25. Gal, A and Nussinovitch, A. 2007. Hydrocolloid Carriers with filler inclusion for diltiazem hydrochloride release. J Pharm Sci. 96(1):168-78. (e-pub date Oct. 9, 2006).

The invention claimed is:

1. A hydrocolloid carrier bead comprising a hydrocolloid polymer and at least one insoluble inert, non-biodegradable filler material, wherein said at least one filler material provides at least one property selected from the group consisting of increased mechanical strength, increased compressibility and reduced porosity compared to a bead having the same composition without said at least one filler, wherein said hydrocolloid polymer comprises a polymer selected from the group consisting of agarose, carrageenan, gellan, and konjak mannan, wherein said hydrocolloid polymer is present in a weight percentage ranging from 1-3% of the wet bead and said at least one filler material is in a weight percentage ranging from 10-15% of the wet bead and from 50-70% (w/w) of the dried bead.

2. The carrier bead according to claim 1, wherein said hydrocolloid polymer comprises agarose in combination with a polymer selected from the group consisting of agar, pectin, carrageenan, alginate, gelatin, gellan, konjak mannan, xanthan gum and locust bean gum.

3. The carrier bead according to claim 1, wherein said hydrocolloid polymer consists of agarose.

4. The carrier bead according to claim 1, wherein said at least one filler material comprises grains in the size of 0.1 μm to 100 μm.

5. The carrier bead according to claim 1, wherein said at least one filler material comprises grains in the size of 0.001 μm to 1 μm.

6. The carrier bead according to claim 1, wherein said at least one filler material is selected from the group consisting of talc, kaolin, calcium carbonate, silicon dioxide, titanium dioxide, alumina, powdered cellulose and microcrystalline cellulose.

7. The carrier bead according to claim 1, further comprising at least one active agent.

8. The carrier bead according to claim 7, wherein said active agent is selected from the group consisting of a medicinally active agent, a chemical or biological agent and an agriculturally active agent.

9. The carrier bead according to claim 8, wherein said active agent is a medicinally active agent selected from the group consisting of a drug, a pro-drug, a combination of drugs, a diagnostic agent and an imaging agent used in therapy or diagnosis.

10. The carrier bead according to claim 9, wherein said active agent is a water-insoluble drug.

11. The carrier bead according to claim 10, wherein said active agent is an agriculturally active agent selected from the group consisting of an agro-chemical compound used for control of pests, a fertilizer and a biological compound.

12. The carrier bead according to claim 11, wherein said active agent is an agriculturally active agent that is other than an active microorganism used for biological control of a pest or a disease.

13. The carrier bead according to claim 7, wherein said at least one filler material comprises a material that is adapted to reduce the rate of the release of said at least one active agent from the carrier bead relative to a bead without said material.

14. The carrier bead according to claim 8, wherein said at least one filler material comprises a material that is adapted to reduce the rate of the release of said at least one active agent by 50% from the carrier bead relative to a bead without said material.

15. A pharmaceutical composition comprising at least one carrier bead according to claim 1.

16. A method for treating a disorder comprising administering the pharmaceutical composition of claim 15 to a subject so as to treat said disorder.

17. The carrier bead according to claim 8, wherein said active agent is a water-soluble drug.

18. A pharmaceutical composition comprising at least one carrier bead according to claim 17.

19. A method for treating a disorder comprising administering the pharmaceutical composition of claim 18 to a subject so as to treat said disorder.

20. A hydrocolloid carrier bead comprising a hydrocolloid polymer, at least one insoluble inert, non-biodegradable filler material, and a water-insoluble drug provided in an oil, a fat or an emulsion, wherein said at least one filler material provides at least one property selected from the group consisting of increased mechanical strength, increased compressibility and reduced porosity compared to a bead having the same composition without said at least one filler, wherein said hydrocolloid polymer is present in a weight percentage ranging from 1-3% of the wet bead and said at least one filler material is in a weight percentage ranging from 10-15% of the wet bead and from 50-70% (w/w) of the dried bead.

* * * * *